(12) United States Patent
Rawlings et al.

(10) Patent No.: US 9,129,059 B2
(45) Date of Patent: *Sep. 8, 2015

(54) ANALYZING ADMINISTRATIVE HEALTHCARE CLAIMS DATA AND OTHER DATA SOURCES

(71) Applicant: OptumInsight, Inc., Eden Prairie, MN (US)

(72) Inventors: Jean W. Rawlings, Roy, UT (US); David R. Anderson, Chaska, MN (US); Carl Kraus, Raleigh, NC (US); Andrew Paris, Victor, NY (US)

(73) Assignee: OPTUMINSIGHT, INC., Eden Prairie, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/185,476

(22) Filed: Feb. 20, 2014

(65) Prior Publication Data

US 2014/0236618 A1    Aug. 21, 2014

Related U.S. Application Data

(63) Continuation of application No. 13/073,573, filed on Mar. 28, 2011, now Pat. No. 8,700,649, which is a continuation of application No. 11/567,577, filed on Dec. 6, 2006, now Pat. No. 7,917,525.

(60) Provisional application No. 60/742,774, filed on Dec. 6, 2005.

(51) Int. Cl.
| | |
|---|---|
| *G06F 19/00* | (2011.01) |
| *G06Q 40/08* | (2012.01) |
| *G06Q 50/22* | (2012.01) |

(52) U.S. Cl.
CPC ............ *G06F 19/36* (2013.01); *G06F 19/3487* (2013.01); *G06F 19/363* (2013.01); *G06Q 40/08* (2013.01); *G06Q 50/22* (2013.01); *Y10S 707/941* (2013.01)

(58) Field of Classification Search
None
See application file for complete search history.

(56) References Cited

U.S. PATENT DOCUMENTS

| | | | |
|---|---|---|---|
| 5,191,522 | A | 3/1993 | Bosco et al. |
| 5,197,024 | A | 3/1993 | Pickett |

(Continued)

FOREIGN PATENT DOCUMENTS

EP    1420344 A2    5/2004

OTHER PUBLICATIONS

Grunwald et al., "Analysis of Genotypic Diversity Data for Populations of Microorganisms," Phytopathology, 93:738-746, 2003.

(Continued)

*Primary Examiner* — Robert Beausoliel, Jr.
*Assistant Examiner* — Susan F Rayyan
(74) *Attorney, Agent, or Firm* — Norton Rose Fulbright US LLP

(57) ABSTRACT

Techniques suitable for identifying potential subjects for a clinical trial and other applications are disclosed. One or more exclusion or inclusion criteria are defined for the clinical trial. One or more specialized searching tables are pre-generated using administrative healthcare claims data and the one or more exclusion or inclusion criteria. The specialized searching tables are searched. Through the searching step, subjects are identified within the administrative healthcare claims data who match the one or more exclusion or inclusion criteria. Through the searching step, a geographical area is identified corresponding to the subjects who match the one or more exclusion or inclusion criteria. A customized report is generated using the identified subjects and geographical area.

23 Claims, 11 Drawing Sheets

(56) References Cited

U.S. PATENT DOCUMENTS

| | | |
|---|---|---|
| 5,557,514 A | 9/1996 | Seare et al. |
| 5,835,897 A | 11/1998 | Dang |
| 5,956,689 A | 9/1999 | Everhart, III |
| 5,970,463 A | 10/1999 | Cave et al. |
| 5,970,464 A | 10/1999 | Apte et al. |
| 6,014,631 A | 1/2000 | Teagarden et al. |
| 6,137,911 A | 10/2000 | Zhilyaev |
| 6,151,581 A | 11/2000 | Kraftson et al. |
| 6,223,164 B1 | 4/2001 | Seare et al. |
| 6,253,186 B1 | 6/2001 | Pendleton, Jr. |
| 6,370,511 B1 | 4/2002 | Dang |
| 6,732,113 B1 | 5/2004 | Ober et al. |
| 6,826,536 B1 | 11/2004 | Forman |
| 2001/0016842 A1 | 8/2001 | Umen et al. |
| 2001/0034631 A1 | 10/2001 | Kiselik |
| 2002/0002474 A1 | 1/2002 | Michelson et al. |
| 2002/0077853 A1* | 6/2002 | Boru et al. ............ 705/2 |
| 2002/0138306 A1 | 9/2002 | Sabovich |
| 2002/0165762 A1 | 11/2002 | Goldman et al. |
| 2002/0173990 A1 | 11/2002 | Marasco |
| 2003/0046114 A1 | 3/2003 | Davies et al. |
| 2003/0071844 A1* | 4/2003 | Evans ............ 345/763 |
| 2003/0191664 A1 | 10/2003 | Blumenfeld |
| 2004/0044654 A1 | 3/2004 | Ballenger et al. |
| 2004/0078216 A1 | 4/2004 | Toto |
| 2004/0078220 A1 | 4/2004 | Jackson |
| 2004/0078236 A1 | 4/2004 | Stoodley et al. |
| 2004/0093240 A1 | 5/2004 | Shah |
| 2004/0153435 A1 | 8/2004 | Gudbjartsson et al. |
| 2004/0172293 A1 | 9/2004 | Bruschi et al. |
| 2004/0191779 A1* | 9/2004 | Zhang et al. ............ 435/6 |
| 2004/0210457 A1 | 10/2004 | Sameh |
| 2004/0220831 A1 | 11/2004 | Fabricant |
| 2004/0236601 A1 | 11/2004 | Summers et al. |
| 2004/0249677 A1 | 12/2004 | Datta et al. |
| 2004/0260577 A1 | 12/2004 | Dahlin et al. |
| 2005/0010443 A1 | 1/2005 | Zammitt |
| 2005/0071189 A1 | 3/2005 | Blake et al. |
| 2005/0114334 A1 | 5/2005 | Ober et al. |
| 2005/0203776 A1 | 9/2005 | Godwin et al. |
| 2005/0228593 A1 | 10/2005 | Jones |
| 2005/0228808 A1 | 10/2005 | Mamou et al. |
| 2005/0234740 A1 | 10/2005 | Krishnan et al. |
| 2005/0234968 A1 | 10/2005 | Arumainayagam et al. |
| 2006/0015325 A1 | 1/2006 | Moore |
| 2006/0101048 A1* | 5/2006 | Mazzagatti et al. ........ 707/101 |
| 2006/0111847 A1* | 5/2006 | Pearson et al. ............ 702/19 |
| 2007/0271214 A1 | 11/2007 | Sumino et al. |

OTHER PUBLICATIONS

Wu, "An Accurate Computation of the Hypergeometric Distribution Function," ACM Transactions on Mathematical Software, 19:33-43, 1993.

* cited by examiner

Acute Coronary Syndrome
Acute Leukaemia's
ADHD
Allergic Rhinitis
Allergy
Alzheimer's Disease
Anemia
Anemia in Cancer Patients
Angina
Anisometropia and/or Amblyopia
Asthma
Benign Prostatic Hyperplasia (BPH)
Bipolar Disorder
Bone Marrow Transplant
Brain Tumors
Breast Cancer (Adjuvant)
Breast Cancer (Advanced/Metastatic)
Bronchitis
Chronic Immune Thrombocytopenic Purpura
Chronic Inflammatory Demyelinating Polyneuropathy
Chronic, Non-Malignant Pain
Congestive Heart Failure
COPD
Coronary Artery Disease
Dementia with Lewy Bodies
Diabetes Diabetic Macular Edema
Diabetic Neuropathy
End Stage Renal Disease
Epilepsy
Erectile Dysfunction
Gastric Symptoms
Gastroenteritis
Gastroesophageal Reflux Disease
Generalized Anxiety Disorder
Glaucoma
Healthy Volunteers (Analgesia)
Hemophilia
Hepatitis B
Hepatitis C
Hormone Replacement Therapy
Human Immunodeficiency Virus (HIV)
Hypercholesterolemia
Hyperlipidemia
Irritable Bowel Syndrome
Major Depressive Disorder
Mesothelioma
Migraine
Mild Cognitive Impairment
Multiple Sclerosis
Myocardial Infarction
Non Small Cell Lung Cancer (NSCLC)

Non-Hodgkins Lymphoma
Obesity
Obsessive-Compulsive Disorder
Oropharyngeal Candidiasis
Osteoarthritis
Overactive Bladder (OAB)
Painful Diabetic Neuropathy
Panic Disorder
Parkinson's Disease
Post-Operative Pain (orthopedic)
Premenstrual Dysphoric Disorder
Prostate Cancer
Psoriasis
Rheumatoid Arthritis
Rhinitis
Schizophrenia
Seasonal Affective Disorder
Sexual Dysfunction
Small Cell Lung Cancer (SCLC)
Smoking Cessation
Social Phobia
Stroke
Systemic Lupus Erythematosis
Tinea Pedis
Ulcerative Colitis
Urinary Tract Infection

FIG. 5

ANALYZING ADMINISTRATIVE HEALTHCARE CLAIMS DATA AND OTHER DATA SOURCES

CROSS-REFERENCE TO RELATED APPLICATIONS

The present application is a continuation of co-pending application Ser. No. 13/073,573, filed Mar. 28, 2011, which is a continuation of Ser. No. 11/567,577, filed Dec. 6, 2006, and now issued as U.S. Pat. No. 7,917,525 which claims the priority of U.S. Provisional Patent Application 60/742,774, filed Dec. 6, 2005, the entire contents of each of which are incorporated herein by reference in their entirety without disclaimer.

COMPUTER PROGRAM LISTING APPENDIX

The computer program listing on the accompanying compact disk is hereby incorporated by reference (Artifact: 14/185476UA, Size: 34.7 KB, Created: Jul. 23, 2015).

BACKGROUND OF THE INVENTION

1. Field of the Invention

The present invention relates generally to data mining and analysis. More particularly, it concerns mining and analyzing medial claims data to, e.g., (a) assist in the identification of clinical investigators and potential trial subjects for clinical trials or determining feasibility of clinical trials, (b) assist in the identification of medical expert witnesses, medical directors, or other medical professionals, (c) assist in the investigation of medical fraud, and (d) assist in various types of marketing. Even more particularly, it concerns improving the speed of medical-related data mining and analysis of very large data sets such as administrative healthcare data through the creation and use of specialized searching tables (SSTs). It also concerns improving the speed of certain statistical calculations through the creation and use of factorial tables having logarithmic entries, making it possible to reliably work with very large numbers and data sets.

2. Description of Related Art

A wealth of information is contained in administrative healthcare claims data. For example, an administrative healthcare claims database may contain information concerning, but not limited to, patient identification, physician identification, physician history, prescription drug history, medical examination history, medical diagnosis history, medical billing history, medical cost information, health benefit information, medical procedures, etc.

Conventional techniques have been employed to mine at least some of this information. Data mining of healthcare claims data, however, involves a slow, computationally-intensive process that may return useful results only after hours or more of computation time. Lengthy search and analysis times plague the medical data mining field and discourage many from fully utilizing medial claims data for useful applications.

Administrative Healthcare Claims Data and Statistical Calculations

Healthcare organizations and many other organizations lack the ability to rapidly analyze extremely large data sets (e.g., over a billion claim lines), apply statistical analysis protocols, and aggregate output into relevant, actionable answers for a specific need.

When working with very large datasets (like administrative healthcare claims data), it is difficult and time consuming to look for patterns that are non-random. Generally speaking, the process sometimes involves comparing each record (for example in a claim) against every other record, keeping track of differences, and then analyzing the differences for patterns. As data sets get larger, there can be an explosion in the number of unique comparisons that need to be made. For example, if one has 10 million records, then adding one record may mean that there will be 10 million new comparisons that need to be made and tracked. When one has 100 million records and 1 record is added, there may be up to 100 million new comparisons to make. As such, there are entire classes of analysis that are impractical or impossible to perform on very large data sets, no matter how powerful the database engine.

Administrative Healthcare Claims Data for Clinical Trials

Clinical trials rely on voluntary participation of study subjects to evaluate new drugs, medical devices, or other interventions. Trials may also be directed to, among other things, evaluating procedures for detecting or diagnosing a particular disease or finding ways to improve the quality of life for those suffering from a chronic illness. Trials are usually conducted by researchers associated in some way with a pharmaceutical company, university, hospital, foundation, or governmental agency.

A significant challenge in carrying out any clinical trial is recruiting the appropriate number and type of volunteer study subjects. Volunteer study subjects are selected so that they meet one or more exclusion or inclusion criteria defined by a study protocol that has been approved by an ethics review board. These criteria are aimed at investigating the impact of a predefined intervention (e.g., a new drug) on a particular patient population (e.g., include only hypertensive patients and exclude those younger than 18) and thereby characterize the effect of such an intervention on this population. This stage of the clinical trial—patient recruitment—can be costly, for each extra day it takes to identify a pool of subjects may ultimately represent one fewer day a new drug is on the market (and protected by a patent or other intellectual property). For some successful drugs, the cost of delay may approach or even surpass millions of dollars per day.

Some have attempted to use administrative healthcare claims data for the recruitment of subjects for clinical trials. Services in existence today involve researchers submitting a clinical trial protocol including related inclusion and exclusion criteria to a data service. The data service accesses administrative healthcare claims data (often of limited scope) in an attempt to estimate the size of a pool of potential study subjects and estimate their location. The service, however, can take upwards of one-month for results to be returned. This time delay comes about, at least partially, due to the large amount of time necessary for the actual data mining and analysis. Because healthcare claims data can involve millions of records, the searching necessary to identify potential study subjects can be very time consuming and can, in some instances, represent a significant time delay in bringing a drug to market. Additionally, the long delay may compound itself if researchers discover that a first set of inclusion/exclusion criteria would not yield a large enough potential study subject pool. When the inclusion/exclusion criteria are modified in an attempt to encompass more participants, the researcher may be forced to wait another month or longer before knowing if the change in criteria will indeed yield an appropriate number of possible study subjects.

Administrative Healthcare Claims Data for Detecting Medical Fraud

Data mining techniques known in the art have been used in an attempt to detect abnormalities in billing practices of physicians, through analysis of underlying claims data. For example, through claims data, one can attempt to determine whether there are any abnormalities or consistent differences in billing practices that would result in higher payments being directed to the physician in question.

Conventional techniques, however, suffer from the same or similar problems discussed above—namely, lengthy analysis times. Additionally, because of the vast amount of data that may be associated with a claims database, traditional techniques have not been able to take advantage of certain statistical techniques that would provide particularly useful information concerning potential fraud. For example, statistical techniques that employ the factorials of extremely large numbers are not undertaken at least because the calculations would cause "data overflow" errors, or other errors that would slow or stop an analysis.

Administrative Healthcare Claims Data for Other Applications

Mining administrative healthcare claims data for other applications suffers similar problems concerning long computation times and delay. The problems are believed to discourage researchers and others from taking advantage of the full potential of claims data.

The referenced shortcomings of conventional methodologies mentioned above are not intended to be exhaustive, but rather are among many that tend to impair the effectiveness of previously known techniques concerning data mining and aggregated analysis of large amounts of healthcare claims data. Other noteworthy problems may also exist; however, those mentioned here are sufficient to demonstrate that the methodology appearing in the art have not been altogether satisfactory and that a significant need exists for the techniques described and claimed here.

SUMMARY OF THE INVENTION

Techniques disclosed here may be used to improve data mining and analysis of administrative healthcare claims data. These techniques are applicable to a vast number of applications, including but not limited to (a) the identification of potential clinical trial investigators, identification of potential subject populations for clinical trial participation or analyzing the feasibility of clinical trials, (b) the identification of medical expert witnesses, medical directors, or other medical professionals, (c) the investigation of medical fraud, and (d) marketing. Medical research applications may also benefit from the techniques of this disclosure. Although focused on administrative healthcare claims data, the same techniques can be applied to other types of data.

In different embodiments, the techniques of this disclosure improve the speed of data mining and analysis of administrative healthcare claims data through the creation and use of specialized searching tables (SSTs). The ability to use certain statistical calculations is provided. Further, those statistical calculations can be accomplished quickly through the creation and use of factorial tables including logarithmic entries, which make it possible to work with very large numbers and data sets. For example, hypergeometric statistical calculations can be performed quicker using these tables than by traditional techniques.

In one respect, the invention involves a computerized method. One or more exclusion or inclusion criteria are defined. One or more specialized searching tables are pre-generated using the one or more exclusion or inclusion criteria. The specialized searching tables are searched. Through the searching step, data is identified within a data set that matches the one or more exclusion or inclusion criteria. Through the searching step, a geographical area is identified corresponding to the data that matches the one or more exclusion or inclusion criteria. A customized report is generated using the identified data and geographical area. The method may also include (a) pre-generating one or more factorial tables, where the factorial tables include logarithmic entries, (b) comparing one or more data records against a plurality of other records, and (c) calculating a hypergeometric statistical result based on the comparing step using the one or more factorial tables.

In another respect, the invention involves a computerized method for identifying potential subjects for a clinical trial. One or more exclusion or inclusion criteria are defined for the clinical trial. One or more specialized searching tables are pre-generated using administrative healthcare claims data and the one or more exclusion or inclusion criteria. The specialized searching tables are searched. Through the searching step, subjects are identified within the administrative healthcare claims data who match the one or more exclusion or inclusion criteria. Through the searching step, a geographical area is identified corresponding to the subjects who match the one or more exclusion or inclusion criteria. A customized report is generated using the identified subjects and geographical area. Defining one or more exclusion or inclusion criteria may include selecting criteria using a Venn diagram. Defining one or more exclusion or inclusion criteria may include selecting one or more medical diagnosis codes. Identifying the geographical area may include identifying a zip code. The customized report may include a map illustrating subjects according to location. The method may also include identifying potential clinical investigators for the clinical trial through searching of the specialized searching tables and generating a customized report using identified investigators and a corresponding geographical area. One or more investigator databases may be used to identify the investigators. The method may also include, prior to the generating of the customized report, defining a minimum subject participation and modifying the one or more exclusion or inclusion criteria if the number of subjects within the administrative healthcare claims data who match the one or more exclusion or inclusion criteria does not meet the minimum subject participation. Such modifying may be done automatically. Such modifying may be done automatically and iteratively until the minimum subject participation is met. This technology may be embodied on a computer readable medium comprising computer executable instructions that, when executed, carry out the techniques described here.

In another respect, the invention involves a computerized method for recruiting a medical professional. One or more exclusion or inclusion criteria are defined for the medical professional. One or more specialized searching tables are pre-generated using administrative healthcare claims data and the one or more exclusion or inclusion criteria. The specialized searching tables are searched. Through the searching step, medical professionals are identified within the administrative healthcare claims data who match the one or more exclusion or inclusion criteria. Through the searching step, a geographical area is identified corresponding to the medical professionals who match the one or more exclusion or inclusion criteria. A customized report is generated using the identified medical professionals and geographical area. Defining one or more exclusion or inclusion criteria may include selecting criteria using a Venn diagram. Defining one or more exclusion or inclusion criteria may include selecting one or more medical diagnosis codes. The medical professionals may include physicians being recruited as an expert witness for litigation. The method may also include determining if one or more of the physicians have previous experience as an expert witness, through correlation with one or more expert databases. This technology may be embodied on a computer readable medium comprising computer executable instructions that, when executed, carry out the techniques described here.

In another respect, the invention involves a computerized method for statistical calculations based on administrative healthcare claims data. Administrative healthcare claims data is searched. One subset of the administrative healthcare claims data is compared against a plurality of other subsets of the administrative healthcare claims data. A hypergeometric statistical result is calculated based on the comparing step using one or more pre-generated factorial tables, the factorial tables including logarithmic entries. Calculating may include one or more calculations using the logarithmic entries followed by one or more exponential operations. The method may also include using the hypergeometric statistical result to detect medical-related fraud. The one subset may include medical coding data associated with a first physician and the plurality of other subsets may include medical coding data associated with a plurality of other physicians. The plurality of other physicians may be selected to be within the same specialty as the first physician. The method may also include generating a customized report comparing the first physician versus the plurality of other physicians. The customized report may include a graph of utilization percentage versus medical code for the first physician and the plurality of other physicians. The method may also include using the hypergeometric statistical result to rate one physician versus other physicians. The method may also include using the hypergeometric statistical result to identify potential subjects for a clinical trial. The method may also include using the hypergeometric statistical result to recruit a medical professional for use as an expert witness for litigation. This technology may be embodied on a computer readable medium comprising computer executable instructions that, when executed, carry out the techniques described here.

In another respect, the invention involves a computerized method, in which one or more specialized searching tables are pre-generated using administrative healthcare claims data. One or more factorial tables are pre-generated, the factorial tables including logarithmic entries. The specialized searching tables are searched. Through the searching step, one or more records are identified within the administrative healthcare claims data that matches one or more search criteria. The one or more records are compared against a plurality of other records of the administrative healthcare claims data. A hypergeometric statistical result is calculated based on the comparing step using the one or more factorial tables. A customized report is generated using the one or more records and the statistical result. The one or more search criteria may include one or more exclusion or inclusion criteria selected using a Venn diagram. The calculating may include one or more calculations using the logarithmic entries followed by one or more exponential operations. This technology may be embodied on a computer readable medium comprising computer executable instructions that, when executed, carry out the techniques described here.

As used in this disclosure, an "inclusion criteria" means a parameter that aims at including certain data in search results. An "exclusion criteria" aims to exclude certain data in search results. Inclusion and exclusion criteria are relative terms— an inclusion criteria may by necessity exclude some data and vice-versa. In general, an exclusion or inclusion criteria is simply a searching parameter. Specifically, exclusion or inclusion criteria can be any parameters that define a search and operate to filter or potentially filter data.

As used in this disclosure the term, "pre-generate" means to generate prior to any searching step.

As used in this disclosure the term, "Specialized Searching Table" or "SST" means a custom, indexed data table organized according to predefined exclusion or inclusion criteria, the indexed table populated with a subset of information from one or more larger tables. The SST is designed to optimize or speed the searching of data, at the expense of added disk space or other memory, for it reproduces a subset of information from one or more larger tables into a separate table that is then searched. One SST can act in concert with one or more other SSTs to achieve a search. Searching of SSTs can be done in parallel, serially, or a combination thereof. In one embodiment, an SST or set of SSTs may be built with or on a FACT table using a concatenated index (an index containing several fields and leading with the appropriate field(s)). In such an embodiment, optimal queries only use the SST index structure and not interact with the FACT table. In this disclosure, SSTs may also be referred to as "packed" tables.

As used in this disclosure, "administrative healthcare claims data" or "healthcare data" is used according to its ordinary meaning in the art and should be interpreted to include, at least, data organized electronically that is searchable via computer algorithm and which contains records associated with one or more medical procedures, prescriptions, diagnoses, medical devices, etc.

As used in this disclosure, "match" in the context of a search should be interpreted to include exact matches as well as substantial matches or matches set up with a pre-defined tolerance.

As used in this disclosure the term, "customized report" means an output (hard-copy or soft-copy) that is individually tailored for the user (e.g., person or entity) through the inclusion of a result or result summary prompted through user input. A customized report need not be unique to a user.

As used in this disclosure the term, "minimum subject participation" is any quantitative measure of a minimum level of participation such as subject total or subject density.

As used in this disclosure the term, "factorial table" is an indexed data table whose entries include factorial values for one or more numbers. In a preferred embodiment, a factorial table is an indexed data table whose entries include logarithmic representations of factorial values for one or more numbers.

The term "code keys," as used herein, represents any desired searchable attribute. In one embodiment, "code keys" may represent diagnosis codes, prescription codes, procedure codes, or medical device codes.

The terms "a" and "an" are defined as one or more unless this disclosure explicitly requires otherwise.

The term "approximately" and its variations are defined as being close to as understood by one of ordinary skill in the art. In one non-limiting embodiment the terms are defined to be within 10%, preferably within 5%, more preferably within 1%, and most preferably within 0.5%. The term "substantially" and its variations are defined as being largely but not necessarily wholly what is specified as understood by one of ordinary skill in the art. In one non-limiting embodiment the terms refer to ranges within 10%, preferably within 5%, more preferably within 1%, and most preferably within 0.5% of what is specified.

The terms "comprise" (and any form of comprise, such as "comprises" and "comprising"), "have" (and any form of have, such as "has" and "having"), "include" (and any form of include, such as "includes" and "including") and "contain"

(and any form of contain, such as "contains" and "containing") are open-ended linking verbs. As a result, a method or device that "comprises," "has," "includes" or "contains" one or more steps or elements possesses those one or more steps or elements, but is not limited to possessing only those one or more elements. Likewise, a step of a method or an element of a device that "comprises," "has," "includes" or "contains" one or more features possesses those one or more features, but is not limited to possessing only those one or more features. Furthermore, a device or structure that is configured in a certain way is configured in at least that way, but may also be configured in ways that are not listed.

The term "coupled," as used herein, is defined as connected, although not necessarily directly, and not necessarily mechanically.

Other features and advantages will become apparent with reference to the following detailed description of specific, example embodiments in connection with the accompanying drawings.

BRIEF DESCRIPTION OF THE DRAWINGS

The following drawings form part of the present specification and are included to further demonstrate certain aspects of the present invention. The drawings do not limit the invention but simply offer examples.

FIGS. 4A-4C are schematic diagrams of a computer software interface suitable for carrying out techniques of this disclosure, in accordance with embodiments of the invention.

FIG. 5 is a list of example indications that can make up a administrative healthcare claims data search criteria, in accordance with embodiments of the invention.

DESCRIPTION OF ILLUSTRATIVE EMBODIMENTS

Embodiments of this disclosure allow for the computerized identification of clinical trial investigators and potential subject populations for a clinical trial, the computerized identification of medical professionals (e.g., as an expert witness for litigation, as a medical director for large hospitals), determining the feasibility of a clinical trial, marketing, and other purposes. Embodiments of this disclosure also allow for the improved calculation of statistical results using, e.g., pre-generated tables and transforming factorial tables into their logarithmic equivalent. The statistical results can be used to further efforts for recruiting, marketing, and other applications.

Figure 1:
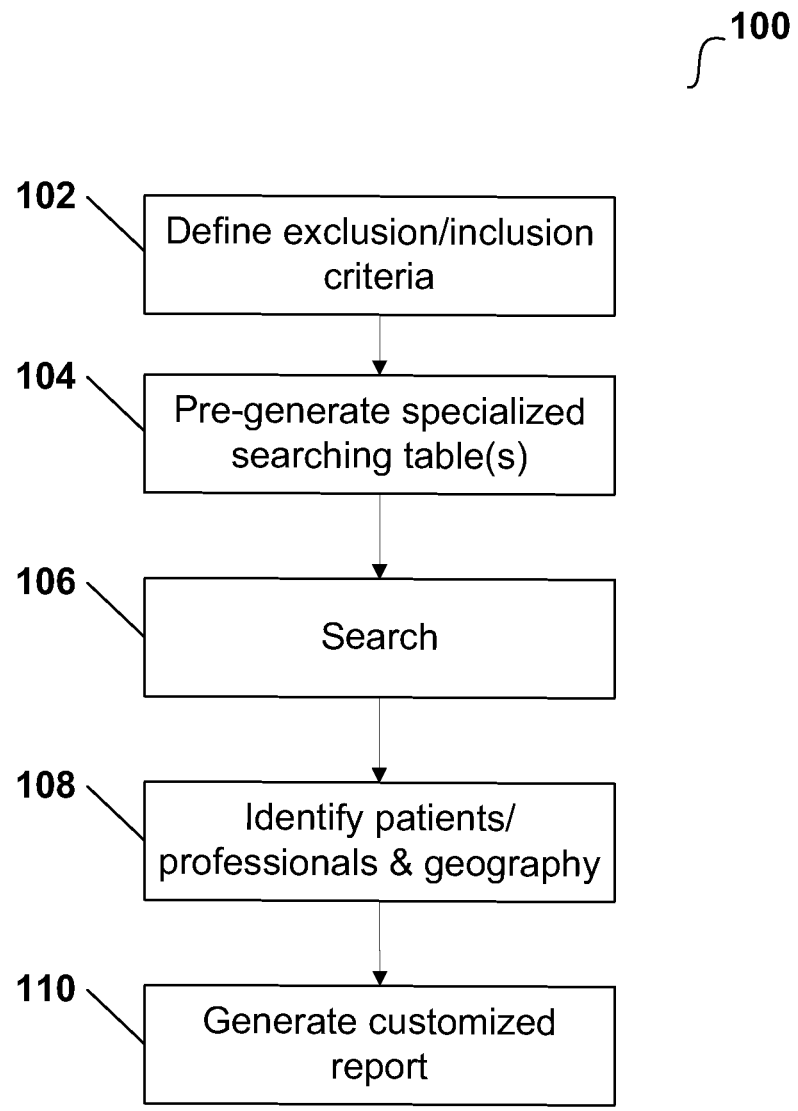
FIG. 1 is a flowchart showing a computerized method for identifying clinical trial investigators and potential subject populations for a clinical trial, for recruiting a medical professional, or for evaluating the feasibility of a clinical trial, in accordance with embodiments of the invention. The steps of FIG. 1 can also be used for other applications.

Turning first to FIG. 1, an example method 100 is shown for identifying clinical investigators and potential subject populations for a clinical trial, determining the feasibility of a clinical trial, or recruiting a medical professional.

Defining Exclusion/Inclusion Criteria

In step 102 of FIG. 1, one or more exclusion or inclusion criteria are defined. In a preferred embodiment, the exclusion or inclusion criteria are designed to correspond to criteria for a clinical trial or other application such as recruiting a medical professional and may include, but are not limited to, desired characteristics of a person (e.g., age, gender, etc.), a targeted health condition (e.g., possessing a certain diagnosis or being associated with a medical diagnosis code, etc.), or an employment characteristic (e.g., medical specialty, etc.). In a preferred embodiment, exclusion or inclusion criteria are defined through direct input from a user. In other embodiments, criteria may be input from other software (e.g., a parameter may be generated in software and output for use in a search). In still other embodiments, criteria may be pre-stored and loaded or otherwise accessed.

Figures 4A, 4B:
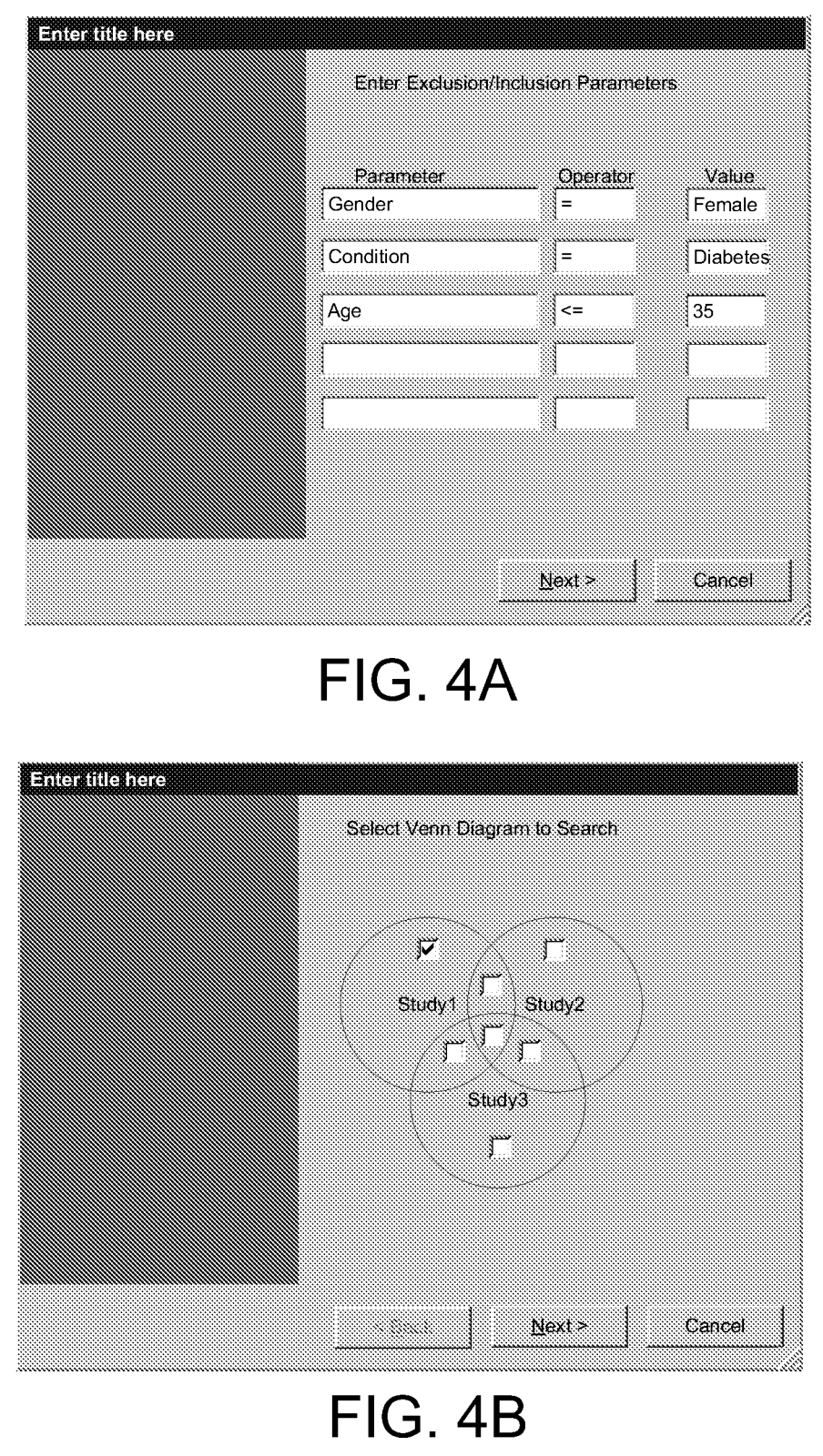

FIGS. 4A-4B illustrate some possible ways in which exclusion or inclusion criteria may be defined via a computer software interface, with direct user input. FIG. 4A presents a "wizard" environment, in which a user is asked to enter exclusion/inclusion criteria by typing one or more parameters along with a respective operator and value.

Criteria may be keywords specifically recognized by software, as shown in FIG. 4A, in which software recognizes the terms "Gender," "Condition," and "Age." In the illustrated embodiment, "Gender" refers to male/female, "Condition" refers to a recognized medical condition, and "Age" refers to the age of a person. In other embodiments, suitable criteria (and optionally, here, medical conditions) may be chosen through a "pull down" or "drop down" list or other mechanism known in the art. For example, one may be presented with a link stating, "List possible criteria." Clicking this link would allow the user to view a list of criteria along with an explanation about each. In different embodiments, the list of criteria may be modifiable by the user, depending on application and depending on the underlying data being searched. For example, if access is provided to a database that has one or more new fields available for search, one may want to add additional search criteria based on those fields. In the embodiment of FIG. 4A, software allows one to enter up to five criteria. In other embodiments, more or fewer may be provided. In other embodiments, the user may specify the number of criteria desired for a particular application. In one embodiment, entire groups of criteria may be defined by a "one-click" or other shortcut manner by, e.g., providing a button or menu that allows a user to define groups of criteria by shortcut name, or through reference to previously-used or saved groups of criteria. If a parameter is not recognized, an appropriate alert or error message may be generated.

Operators suitable for use in the illustrated embodiment of FIG. 4A include, but are not limited to, an equal sign (=), the greater-than sign (>), and the less-than sign (<). These operators act on, or modify the "value." In other embodiments, the operator can be any mathematical or logical operator known in the art to assist in searching. For example, standard or customized Boolean-type operations may be permitted. As shown in FIG. 4A, the operator for the first and second criteria is the equal sign (=), and the operator for the final parameter is the less-than-or-equal-to combination (<=). If an operator is not recognized, an appropriate alert or error message may be generated.

The "value," acting with the operator and criteria, establishes what search is to be performed. In FIG. 4A, the first, second and thirds values are, respectively, Female, Diabetes, and 35. Accordingly, the type of search the user may be interested in involves people who are female, are associated with the Diabetes medical condition, and who are 35 years old or younger. In one embodiment, values are entered directly by a user. In other embodiments, values may be pre-stored and loaded for use, selected individually or in groups, or otherwise entered. FIG. 5 is a list of example indications that can act as a value for a criteria such as "Condition," which is shown in FIG. 4A. More or fewer indications could be used in other embodiments.

Figure 6:
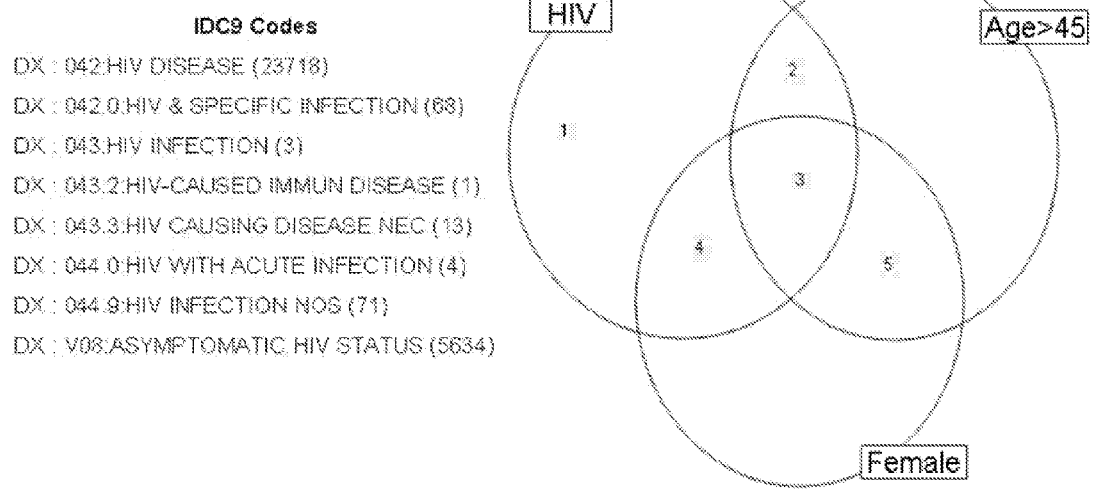
FIG. 6 is a schematic diagram illustrating how one or more exclusion or inclusion criteria can be selected using a Venn diagram, in accordance with embodiments of the invention.

FIG. 6 indicates another example method by which one may define a value for a criteria—here, through the use of accepted medical codes or medical diagnosis codes, such as IDC9 codes. Specifically, to establish a value for a criteria such as "Condition," one may enter one or more IDC9 codes to help identify what condition is of interest. In the embodiment of FIG. 6, eight different IDC9 diagnosis codes are being used to define an HIV exclusion or inclusion criteria, which is represented by the upper left circle of the Venn diagram of FIG. 6. In different embodiments, software may help users look-up appropriate codes to aid in the searching process. For example, if a user wants a search to involve hepatitis, one may look-up all medical diagnosis codes pertinent to all forms of hepatitis. The user may then select from the look-up results to define exclusion or inclusion criteria, and particularly, values for condition-related criteria.

A Venn diagram or other technique may be used to help the user define or visualize exclusion or inclusion criteria. FIG. 4B illustrates using a Venn diagram for this purpose. The Venn diagram of FIG. 4B is used in conjunction with defining exclusion or inclusion criteria and appears in a "wizard" screen that is called once the user selects "Next" after setting up criteria, operators, and values in FIG. 4A. The Venn diagram of FIG. 4B includes three circles, corresponding to the criteria previously defined in FIG. 4A and an additional two studies or groups. In this embodiment, each complete list of inclusion/exclusion criteria creates one Venn diagram. The Venn diagrams allow users to overlap multiple studies or groups. Thus, the first circle in FIG. 4B corresponds to the entire set of criteria listed in FIG. 4A—Females with Diabetes age 35 or younger. The second circle in FIG. 4B would correspond with another study—for example, people with hypertension and hepatitis. The third circle in FIG. 4B would correspond with yet another study, trial, or protocol—for example, children under the age of 12 who have received gamma. The Venn capability provides the ability to identify clinical investigators and potential patient populations who reside in the intersection of these three separate studies. The result may therefore be a list of providers who treat one or more patients who are female with diabetes who have hypertension and have had hepatitis who are under 12 and have received a gamma shot. This ability allows users to establish completely separate protocols for different drugs and to combine protocols in the future for new drugs and/or different indications (potentially identifying off label use, etc.)

Of course, a different number of criteria would lead to a different Venn diagram, with different labels. The Venn diagram allows the user to tailor a search according to any of the exclusion or inclusion criteria alone or in any combination with other exclusion or inclusion criteria. In the illustrated embodiment of FIG. 4B, there are seven different possibilities for searching, represented by the seven different checkboxes presented to a user. Here, by way of example only, the user has selected a search aimed at uncovering data that satisfies the Gender criteria (i.e., Female), the "Condition" criteria (i.e., HIV), and the Age criteria (i.e., 35 years old or younger). Had the user wished to search a different combination, he or she could have checked a different box. Additionally, a user may wish to chose more than one box to determine, e.g., the difference in the number of search "hits" that would result if different exclusion or inclusion criteria combinations are considered. If more than one box is checked, search output may be arranged or formatted to indicate the search results corresponding to each check box.

FIG. 6 illustrates another Venn diagram that can be used to assist in setting up exclusion or inclusion criteria. There, the criteria involved are similar to those of FIG. 4B—they are HIV, age greater than 45, and Female. Five of the seven possible combinations of criteria are numbered. In FIG. 6, different medical codes associated with HIV are given at left (e.g., code 042 for HIV). In FIG. 6, the numbers in parenthesis (e.g., 23718) are counts in the searched member population that have the particular Dx/Rx/Px.

In one embodiment, the exclusion or inclusion criteria may be chosen to satisfy conditions of a clinical trial so that one may recruit subjects (e.g., so that one may, through the searching process, identify patients who would meet the clinical trial criteria). For example, if a researcher is recruiting patients for a drug study and desires volunteer patients over the age of 40 who have asthma but who are not taking a particular class of blood-pressure medications, those criteria may be entered.

In one embodiment, the criteria may be model criteria, chosen by the researcher simply to see if there would be a suitable subject pool if the model criteria were, in fact, actual requirements. In other words, criteria may be set up to model a clinical trial for potential subject identification. Such modeling may be used to provide a list of potential suggestions that could be implemented to meet clinical trial enrollment targets. Such modeling, discussed more below, may also allow a user to check on whether an investigator's enrollment predictions seem reasonable as well as provide temporal and geographic data on targeted enrollment. Additionally, modeling may allow a user to evaluate whether, based on patient base attrition, an investigator is likely to retain study trial subjects.

In another embodiment, the exclusion or inclusion criteria may be chosen to satisfy job conditions so that one may recruit a medical professional. For example, one may define exclusion or inclusion criteria to find a suitable medical expert witness for litigation. If litigation involves esophagus injuries associated with screws backing out from an anterior cervical plate, one could define exclusion or inclusion criteria designed to locate a surgeon who has performed over 100 cervical plate procedures during the past five years. If one believes that a female expert would "connect" more with the jury, one could define a Gender criteria to be equal to Female. If one believes that the expert witness should be from Texas, one could set a Medical School criteria to be equal to one or more Texas schools. If one believes that an expert in the 45-65 age range would have the most credibility, an age criteria could be entered accordingly. In the same manner, one could tailor a search according to any desire, and limited only by the underlying data being searched. As with the clinical trial recruitment embodiment, one may define exclusion or inclusion criteria to simply satisfy different "what if" scenarios—for example, "what if" I was looking for a male expert witness, age 52-55, who went to Baylor College of Medicine, and who has done over 400 cervical plate procedures—how many such people could I possibly identify? If the answer is zero or extremely low, one may realize that expectations need to be modified.

In another embodiment, the exclusion or inclusion criteria may be chosen to satisfy job conditions so that one may recruit a medical professor, executive, researcher, etc. For example, one may define exclusion or inclusion criteria to find an executive with particular experience as a physician working with certain conditions.

These examples illustrate that it may be beneficial to combine data from one database with that of others so that additional criteria may be defined and used for various applications. For example, in the clinical trial recruitment applications, it may be beneficial to use information that identifies physicians as being past investigators for clinical trials so that one may identify not only volunteer study subjects, but also appropriate physicians with experience with trials. This may be accomplished by linking administrative healthcare claims databases with, for instance, an FDA-related database. Additionally, one may identify medical professionals who have testified at trial or deposition by correlating a physician match from a administrative healthcare claims database with a database that keeps track of expert witness experience.

Pre-Generating Specialized Searching Tables

In step 104 of FIG. 1, specialized searching tables (SSTs) are pre-generated. The SSTs of the present disclosure offer significant benefits in the area of administrative healthcare claims data searching as well as other fields at least because of the marked improvement in searching speed and any associated analysis—albeit at the expense of using more disk space (or other computer memory) and the time associated with pre-generating the tables themselves, which may be done at off-peak times, if desired. In one embodiment, over 18 million patient healthcare claims histories, resulting in over 410 million records, may be "packed" into SSTs to greatly improve data mining and analysis.

In one embodiment, SSTs may be pre-generated and used as follows. In this example, "code keys" represent any desired searchable attribute including, but not limited to, Diagnosis codes, Prescription codes, Procedure Codes, etc. In this example, temporal information may also be utilized (e.g., service date) to define encounters in the data set. Those having ordinary skill in the art, having the benefit of this disclosure, will recognize that other types of information may be included for SSTs, according to need. The steps below represent an example only.

Creating SSTs

1. CREATE TABLE PACKED_TABLE as SELECT or INSERT /*+append*/ . . . select distinct code_key, sex, birth date, geographic region, individual_id from fact table of other large table . . . . ORDER BY code_key, sex, birth date, geographic region, individual_id setting appropriate block parameters to 0 space for updates 2. Index the PACKED_TABLE by code_key
    a. alternate 1: create concatenated index on large table leading with code_key and containing all required fields.
    b. Alternate 2: create stand alone index organized table leading with code_key and containing all required fields.

Access SSTs 1. set#1 is SELECT sex, birth date, geographic region, individual_id from PACKED_TABLE where code_key in (code_key1a,code_key2a,etc)

2. set#2 is SELECT sex, birth date, geographic region, individual_id from PACKED_TABLE where code_key in (code_key1b,code_key2b,etc)

3. set#N is SELECT sex, birth date, geographic region, individual_id from PACKED_TABLE where code_key in (code_key1X,code_key2X,etc)

4. The sets can then be combined via INTERSECT, UNION, MINUS, etc. to yield results corresponding to any/all Venn region(s). Patient demographic summaries can also be calculated rapidly without requiring joins.

The SSTs of this disclosure can overcome a number of performance obstacles in both the gathering and the processing of large data sets for, e.g., real time statistical probability analysis (a.k.a. signal detection). This method can also contain temporal information (e.g., service date) to define encounters in the data set. Standard warehouse structures hold vast amounts of data and allow access to specific records via bitmapped indexes. However, when large population sets are desired, the shear number of disk seeks required via the bitmapped indexes becomes prohibitive for real-time processing. A solution provided herein is to use SSTs (or standard tables loaded and indexed in a particular way) where each block of each table is rich with the desired information. In other words, if one is searching for possible patients who have had at least one of a set of 10 diabetic medical codes, the user may be directed to a table which contains rows packed by codes. Each physical block read (disk seek) may contain hundreds of the desired individuals, whereas in a standard warehouse a block read will certainly hold at least one desired individual but likely, at most, only a few as dictated by chance.

The SSTs of this disclosure can also overcome statistical processing challenges present in traditional data mining operations. Statistical processing challenges can be encountered once individuals "in play" are ferreted out. For example, if checking for drug safety signals, each attribute of each individual "in play" must be accessed. Also, each outcome for these individuals must be accessed. These two sets may then be permeated against each other, one individual at a time. This process is repeated for each "in play" individual, and the cumulative set is then aggregated for each outcome for each base condition, for each drug in the pairing. For weak filters (filters than don't appreciably narrow the population) this can be a time consuming process. To alleviate this, and according to embodiments of this disclosure, all possible permutation sets may be pre-generated and "packed" by individual IDs into an SST. The "in play" population may then be extracted from the pre-generated SST for aggregation.

Techniques of this disclosure may be advantageously applied to a wide variety of "raw data" to be searched, a preferred embodiment involving administrative healthcare claims data. For example, SSTs can act on virtually any data to improve searching and analysis, and particularly administrative healthcare claims data, regardless of the format and size of the data being mined. In one embodiment, administrative healthcare claims data may be housed on computer servers or other storage devices at one physical location, while in other embodiments, the data may be dispersed about many locations. The data may be accessible via network. The data may be in one or more different formats or layouts. Advantageously, the techniques of this disclosure can lay on top of virtually any data, and the data can be linked together from a variety of sources. Because of inherent TCP transport delays, when dealing with large amounts of data spread across multiple platforms, there is a performance advantage to ensuring that each platform's SST data set be self contained in the sense that only aggregated values are passed to an application server, client or master database server. SSTs have significant performance benefits whenever data sets are primarily accessed by a non-unique field.

SSTs can be updated in a number of ways. In one embodiment, this activity may be done off hours. Updating may be done as follows, which are examples only:

1. Completely reprocess the SST from a FACT table each load cycle.
2. INSERT /*+APPEND*/ the new data into the existing table in the desired order. This will not "pack" as tightly as a complete reprocess but will still have most of the performance advantages provided by this disclosure.

Significant storage benefits can be reaped if the database in use allows field compression on leading and even non-leading index fields. Depending on the packing method used, indexes may be dropped prior to loading and re-created post-load. Or, indexes may be allowed to grow during the load process. However, repeated loads (and deletions) can have detrimental effects on index efficiency.

Searching the SSTs

In step 106 of FIG. 1, the SSTs are searched. The searching step involves the use of the SSTs to filter the underlying administrative healthcare claims data (or other data being searched) according to the exclusion or inclusion criteria defined by the user, and which may be associated with a Venn diagram or other tool. The searching step itself may be carried out according to techniques known by those of ordinary skill in the art.

In one embodiment, searching may be carried out using the techniques of the following example. In this example, one might be interested in determining how many physicians have treated a specific set of diagnoses in a certain way during an encounter (with a specific class of drugs and specific set of procedures) and how many patients each physician has treated in that way, total encounters by physician. This or a similar embodiment may be framed as shown in the following non-limiting scenarios:

1. One class of search only requires that the patient have had certain Dx, Px and Rx codes during an interval regardless of the intervals between the codes (e.g., in the last year which patients have had procedure "A" and drug "B").
2. Another class of search imposes temporal restrictions on the order and interval between the Dx, Px and Rx codes. A temporal example might be: A novel treatment approach for disease "X" (coded as x1, x2, or x3) is procedure "Y" (coded as y1 or y2) and drug "Z" (coded as z1 or z2). One may define this novel treatment as belonging to an "encounter," which may require the diagnosis "X" to occur on or before "Y" and "Z," and furthermore, "Y" must take place on at most 1 day after "X," and "Z" must be filled on or at most 2 days after "X". Now, one may find all patients who have had disease "X" in any of its x1, x2 or x3 forms who were treated with procedure "Y" in forms y1 or y2 within 1 day and filled drug "Z" in forms z1 or z2 within 2 days.
3. This logic can be further extended into an "episode" where the procedure "Y" might have a much longer interval of treatments and even numerous treatments over this longer interval (same with drug "Z").

Regardless of the logic, an output common to all three may be, in one embodiment: Count the unique patients that fit this logic, identify and count the providers that treat patients this way; which providers do this treatment the most often, and which providers do not treat patients this way.

One might also be interested in the demographics of the patient population that has participated in three code sets even if they did not happen in the same encounter. In this example one may create two SST structures (this could be done in one denormalized SST with a moderate performance hit due to increased row length).

Some fields in this example are shown with "natural" values although it is generally desirable to use surrogate keys of the smallest possible length for the desired criteria. After aggregation, the surrogate keys may be joined to descriptive fields.

Demographics of the patient population that has participated in all three code sets even if they did not happen in the same encounter:

```
SST#1 code_key, birth date, geo region, sex, individual_id Ordered
    by code_key
indexed by code_key
    -- tally by gender breakout, age and region are similar
    Select sex, count(unique individual_id) unique_patients from
    (
    Select birth date, geo region, sex, individual_id from SST#1 where
        dx IN
(Dx1,Dx2,...)
    INTERSECT
    Select birth date, geo region, sex, individual_id from SST#1 where
        px IN
(Px1,Px2,...)
    INTERSECT
    Select birth date, geo region, sex, individual_id from SST#1 where
        px IN
(Rx1,Rx2,...)
    ) group by sex
```

Note: when available, temporary holding structures (e.g., global temp tables, WITH temp AS, etc.) can avoid multi-sourcing. Analytic functions can also be used.

Example of Multi-Sourcing from a Single Temp Structure

```
WITH temp AS
    (
        SELECT /*+ first_rows*/
            b.*
        FROM (SELECT /*+ index(a)*/
                individual_id
            FROM MASTER_R1D a
            WHERE a.code_key IN
                ('DX8648571',
                'DX864857481',
                'DX864857491',
                'DX864857501',
                'DX864857511',
                'DX864857521',
                'DX864857531',
                'DX86485753481',
                'DX86485753491',
                'DX864857541',
                'DX864857551',
                'DX86485755481',
                'DX86485755491',
                'DX864857561',
                'DX86485756481',
                'DX86485756491',
                'DX864857571',
                'DX86485757481',
                'DX86485757491',
                ''
                )
        INTERSECT
        SELECT /*+ index(a)*/
            individual_id
        FROM MASTER_R1D a
        WHERE a.code_key IN
            ('PX48485354541',
            'PX51515349481',
            'PX51515349491',
            'PX51515349501',
            'PX51515349511',
```

```
                    'PX51515349521',
                    'PX51515349541',
                    'PX51515349551',
                    'PX51515349561',
                    'PX51515349571',
                    'PX51515350491',
                    'PX51515350501',
                    'PX51515350511',
                    'PX51515351511',
                    'PX51515351521',
                    'PX51515351531',
                    'PX51515351541',
                    ''
                )
            INTERSECT
            SELECT /*+ index(a)*/
                    individual_id
                FROM MASTER_R1D a
                WHERE a.code_key IN ('RX-ZITHROMAX', '')) a,
            INDIVIDUAL_ID_R1D b
        WHERE a.individual_id = b.individual_id)
SELECT -1 ord, 'Male' ATTRIBUTE, SUM (CASE
                                        WHEN gender = 'M'
                                            THEN 1
                                            ELSE 0
                                    END) counts
    FROM temp
UNION ALL
SELECT -2 ord, 'Female' ATTRIBUTE,
        SUM (CASE
                WHEN gender = 'F'
                    THEN 1
                    ELSE 0
            END) counts
    FROM temp
UNION ALL
SELECT *
    FROM (SELECT rn, rn_chr ATTRIBUTE, counts
            FROM (SELECT TO_CHAR (TRUNC ((SYSDATE - dob) /
                365.25)
                                ) ATTRIBUTE,
                        COUNT
                            (UNIQUE CASE
                                WHEN gender = 'M'
                                    THEN individual_id
                                    ELSE NULL
                                END
                            ) counts
                    FROM temp
                GROUP BY TO_CHAR (TRUNC ((SYSDATE -
                    dob) / 365.25))) a,
                YEARS b
            WHERE b.rn_chr = a.ATTRIBUTE(+)
        ORDER BY b.rn ASC)
UNION ALL
SELECT *
    FROM (SELECT rn + 500, rn_chr ATTRIBUTE, counts
            FROM (SELECT TO_CHAR (TRUNC ((SYSDATE -
                dob) / 365.25)
                                ) ATTRIBUTE,
                        COUNT
                            (UNIQUE CASE
                                WHEN gender = 'F'
                                    THEN individual_id
                                    ELSE NULL
                                END
                            ) counts
                    FROM temp
                GROUP BY TO_CHAR (TRUNC ((SYSDATE -
                    dob) / 365.25))) a,
                YEARS b
            WHERE b.rn_chr = a.ATTRIBUTE(+)
        ORDER BY b.rn ASC)
UNION ALL
SELECT *
    FROM ((SELECT 1000 rn,
                'ZIP-3:'
                || SUBSTR (zipcode, 1, 3)
                || ' '
                || TRIM (city)
                || ','
                || state ATTRIBUTE,
                COUNT (UNIQUE individual_id) counts
            FROM temp, ZIP3
            WHERE SUBSTR (zipcode, 1, 3) = ZIP3
        GROUP BY 1,
                'ZIP-3:'
                || SUBSTR (zipcode, 1, 3)
                || ' '
                || TRIM (city)
                || ','
                || state)
    ORDER BY counts DESC);
```

Determining how Many Physicians have Treated a Specific Set of Diagnosis in a Certain Way During an Encounter (with a Specific Class of Drugs and Specific Set of Procedures) and how Many Patients Each Physician has Treated in that Way, Total Encounters by Physician

```
SST#2 code_key, individual_id, encounter date, provider_key
    ordered by
code_key indexed by code_key
    Select provider_key,count(unique individual_id)
    unique_patients,count(unique
individual_id||encounter_date) total_encounters from
    (
    Select individual_id, encounter date, provider_key from SST#2
    where dx IN
(Dx1,Dx2,...)
    INTERSECT
    Select individual_id, encounter date, provider_key from SST#2
    where px IN
(Px1,Px2,...)
    INTERSECT
    Select individual_id, encounter date, provider_key from SST#2
    where px IN
(Rx1,Rx2,...)
    ) group by provider_key
```

In one embodiment, SSTs may also work together. Consider a query where one wants to know the ensuing "play-out" after an individual has had a particular Diagnosis, procedure or drug:

Table SST#3 is code_key, individual_id, encounter_date ordered by code_key,individual_id and indexed by code_key Table SST#4 is individual_id,encounter_date,code_key ordered by individual_id, encounter_date and indexed by individual_id Then the combined query becomes (one of ordinary skill in the art will recognize that they are many ways to write the SQL):

Select SST#4.* from SST#4,(Select individual_id,min(encounter_date) first_encounter from SST#3 group by individual_id) iv where SST#4.individual_id=iv.individual_id and SST#4.encounter_date>iv.first_encounter Searching times of course depend on the amount of data involved. However, using SSTs can dramatically cut searching time to a degree where once-impossible or impracticable tasks can be completed—e.g., identification of clinical investigators and potential subject populations for clinical trials in a quick enough manner so that exclusion or inclusion criteria can be modified "on the fly" in an attempt to establish appropriate protocols with a feasible subject pool.

To highlight performance difference versus existing warehouse techniques, consider the following example query:

```
Select sex, count(unique individual_id) unique_patients from
(
    Select birth date, geo region, sex, individual_id from SST#1 where
    dx IN
(Dx1,Dx2,...)
    INTERSECT
    Select birth date, geo region, sex, individual_id from SST#1 where
    px IN
(Px1,Px2,...)
    INTERSECT
    Select birth date, geo region, sex, individual_id from SST#1 where
    px IN
(Rx1,Rx2,...)
) group by sex
```

To accommodate itemized costs by procedure and the fact that hundreds of procedures may sometimes define an encounter, administrative healthcare claim tables generally contain a single procedure per line with other fields holding diagnosis codes or pointers to a table listing the diagnosis codes associated with the encounter. Prescription data is often, but not always, held in a separate table. Bitmapped indexes are not tailored to this class of problem because they cannot be directly merged/ANDed to narrow the output set prior to table access because the codes are not required to be resident on the same line, only on the same patient. Building a claim table holding every triplet permutation over the covered patient interval could leverage bitmapped index power but would be cause the table to be prohibitively large for anything but a small subset of the population. Likewise "x-walking" columns into a single table is not practical when hundreds of codes are possible in an covered period.

So, for a generic claims table containing
Individual_id, Px1, Dx1, Dx2, Dx2, etc.
And pharmacy table containing
Individual_id, Rx1, etc
The warehouse version of the query becomes:

```
Select p.sex,count(unique individual_id) unique_patients from
(
    Select individual_id from big_claim_table where px1 in
    (Px1,Px2,...) -- we
must pull this set independently since they may not occur on the same
line/encounter as
the Dx codes
    INTERSECT
    Select individual_id from big_claim_table where (dx1 IN
    (Dx1,Dx2,...) OR dx2
in (Dx1,Dx2,...) OR dx3 in (Dx1,Dx2,...)
    INTERSECT
    Select individual_id from big_pharmmacy_table where rx1 in
    (Rx1,Rx2,...)
) iv ,patient_lu p where iv.individual_id=p.individual_id group by
sex
```

This query run on modest code sets compares as follows:

| Data Structure | Physical I/Os | Time to run |
| --- | --- | --- |
| Warehouse | 400000 | 1000 seconds |
| SST | 3300 | 10 seconds |

Or 100 times faster.

Identifying Patients, Professionals, Geography, and Other Results

In step 108 of FIG. 1, searching yields an identification of data matching the exclusion or inclusion criteria previously defined. Any data fields, portions of data fields, or combinations of data fields may be identified in response to the search. In one embodiment, the identification of data comes about through an exact match with search criteria. In other embodiments, a search "hit" may result if there is an approximate or substantial match. For instance, if an exclusion or inclusion criteria seeks physicians who have treated 200 patients having a particular diagnosis, one embodiment would return information for physicians who have treated, e.g., 195 patients. Non-exact matches such as these can be indicated accordingly on a customized report. In one embodiment, the tolerance required to constitute a match may be defined by the user, and the tolerance may be different for different searching criteria.

In one embodiment, patients are identified who may be suitable candidates for a clinical trial, for which clinical trial exclusion or inclusion criteria were defined. In another embodiment, patients are identified for a clinical trial model, in order to determine the number of patients and in order to determine if exclusion or inclusion criteria should be modified to identify even more potential clinical investigators and study subject populations. In another embodiment, one or more medical professionals are identified. For example, a potential medical expert witness, professor, researcher, etc. may be identified.

In one embodiment, information regarding one or more geographic regions is also identified in response to a search. In addition to information that identifies a potential clinical investigator, study subject, or medical professional, the individual's detailed location may be also be identified. The identification of geographic information may be done automatically, with or without the user setting up a geographical search parameter. For example, if the only exclusion or inclusion criteria specified by a user involved the age of a patient, a search may nevertheless return information not only identifying patients matching the age limitation, but also identifying a general geographical region where those patients live. Such information may be pulled from a claims database or other data source being searched. As described more below, the geographic area information may be used advantageously to present search results in map-format.

In one embodiment, identification of individuals through searching is done without revealing any sensitive or protected material. In other words, the techniques of this disclosure may be used in a manner that would not violate privacy rules or laws (e.g., HIPAA regulations). Searching can take place on data that has been "de-identified" to remove reference to, e.g., patient names and social security numbers. Alternatively, searching can take place on original data and then de-identified so that privacy guidelines are met. Techniques known in the art may be used for the de-identification process.

Additional example situations involving the identification of information through searching, and particularly through searching using SSTs are provided below. Those having ordinary skill in the art will recognize that the techniques of this disclosure can be used to identify information for a multitude of other applications, encompassed by the claims.

Generate Customized Report

Figure 4C:
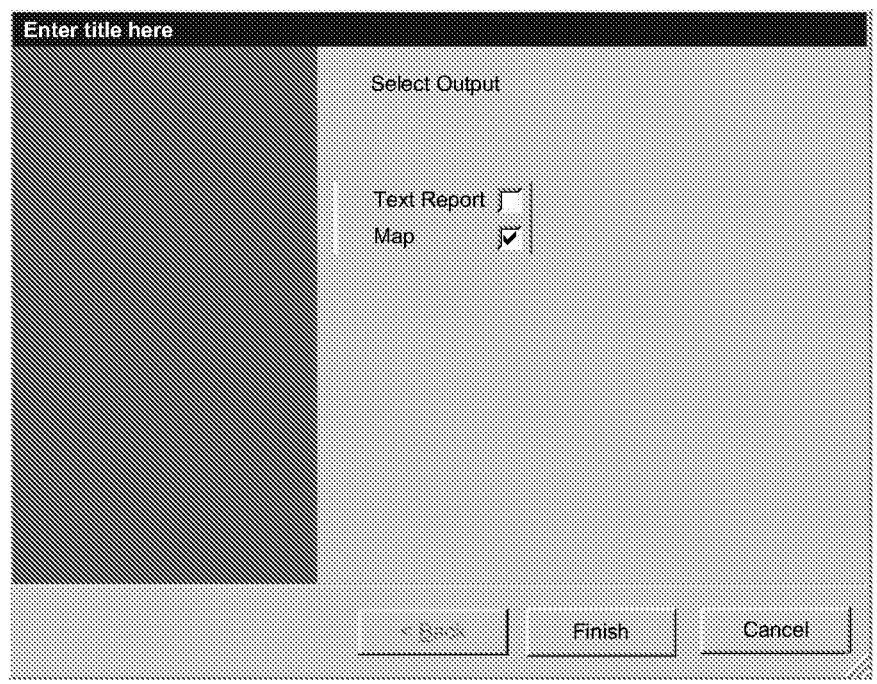

In step 110 of FIG. 1, a customized report is generated. The arrangement and format of the customized report may be dictated by the underlying application and desires of the user. In one embodiment, however, one may wish to choose between textual and map-based reports. In FIG. 4C, such a choice is presented to a user through the "wizard" interface discussed previously. Here, a user can check for a text report or a map.

A text report may be set up to show the exclusion or inclusion criteria at issue, the search results themselves in columnar or other convenient format, and other information (automatically generated or chosen by the user) that may be pertinent to the analysis. Text reports need not be text-only. A text report can include graphics in the form of pictures, graphs, charts, or the like. A customized report may, if desired, be entirely graphical. Reports may be electronic (e.g., on a computer screen) and may include video clips, animations, or the like.

Figure 7:
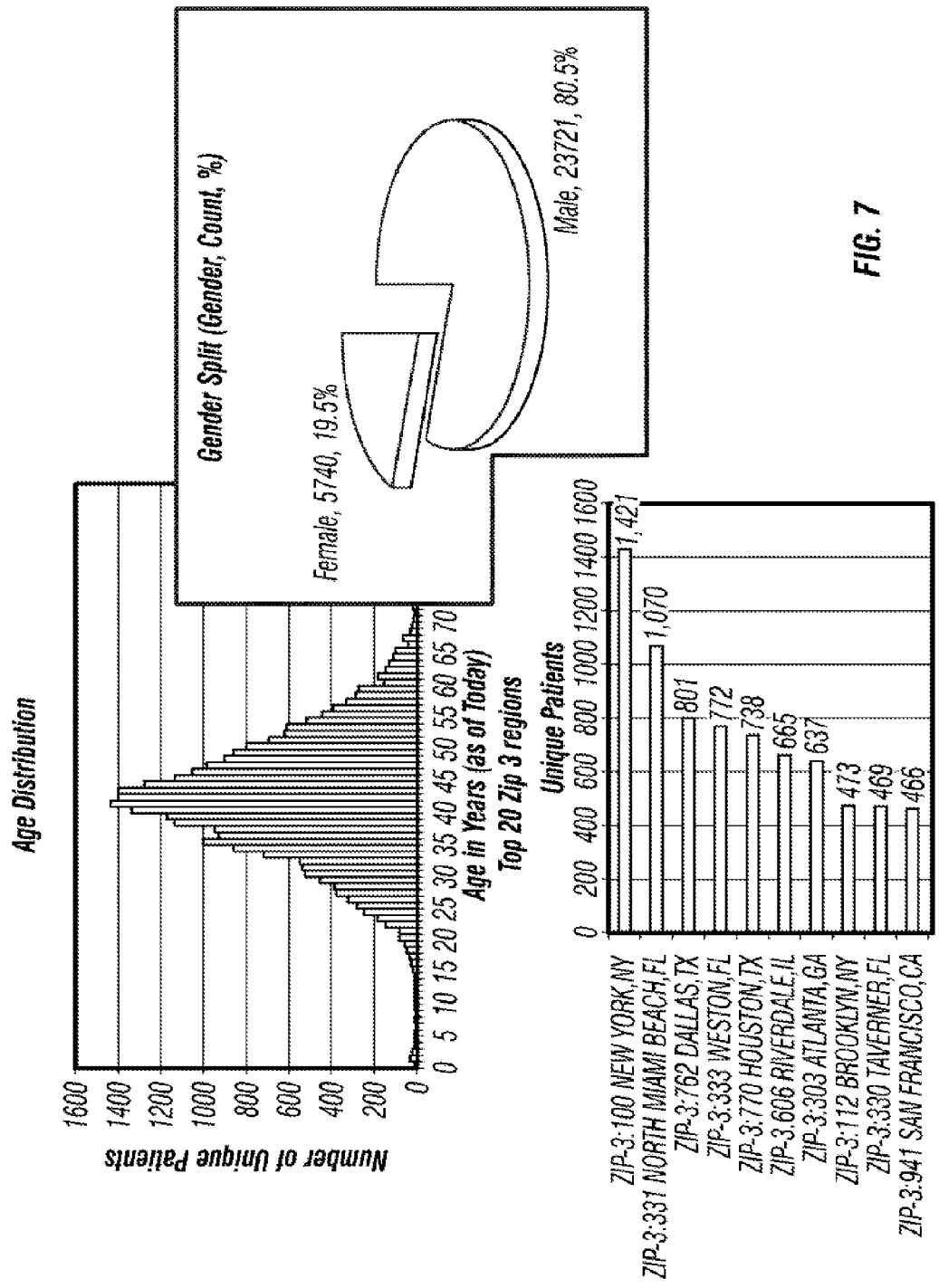
FIG. 7 is a schematic diagram illustrating example customized reports, in accordance with embodiments of the invention.

FIG. 7 shows example customized reports, which are mixed text and graphics. In the upper left, a graph shows the number of unique patients (e.g., potential subjects for a clinical trial matching pre-defined exclusion or inclusion criteria) versus age in years. A quick glance at the graph would reveal to a user that potential subject populations are centered around an age of approximately 42. At the middle-right of FIG. 7 is a graph showing the gender split for the identified patients. Here, over 80% of potential trial subjects are male. At the lower left of FIG. 7, geographical information is presented, but not in the form of a map. Unique subjects are charted as a function of their 3-digit zip code, which reveals that New York, N.Y. may be a suitable site for clinical investigator and trial subject recruitment.

Figure 8:
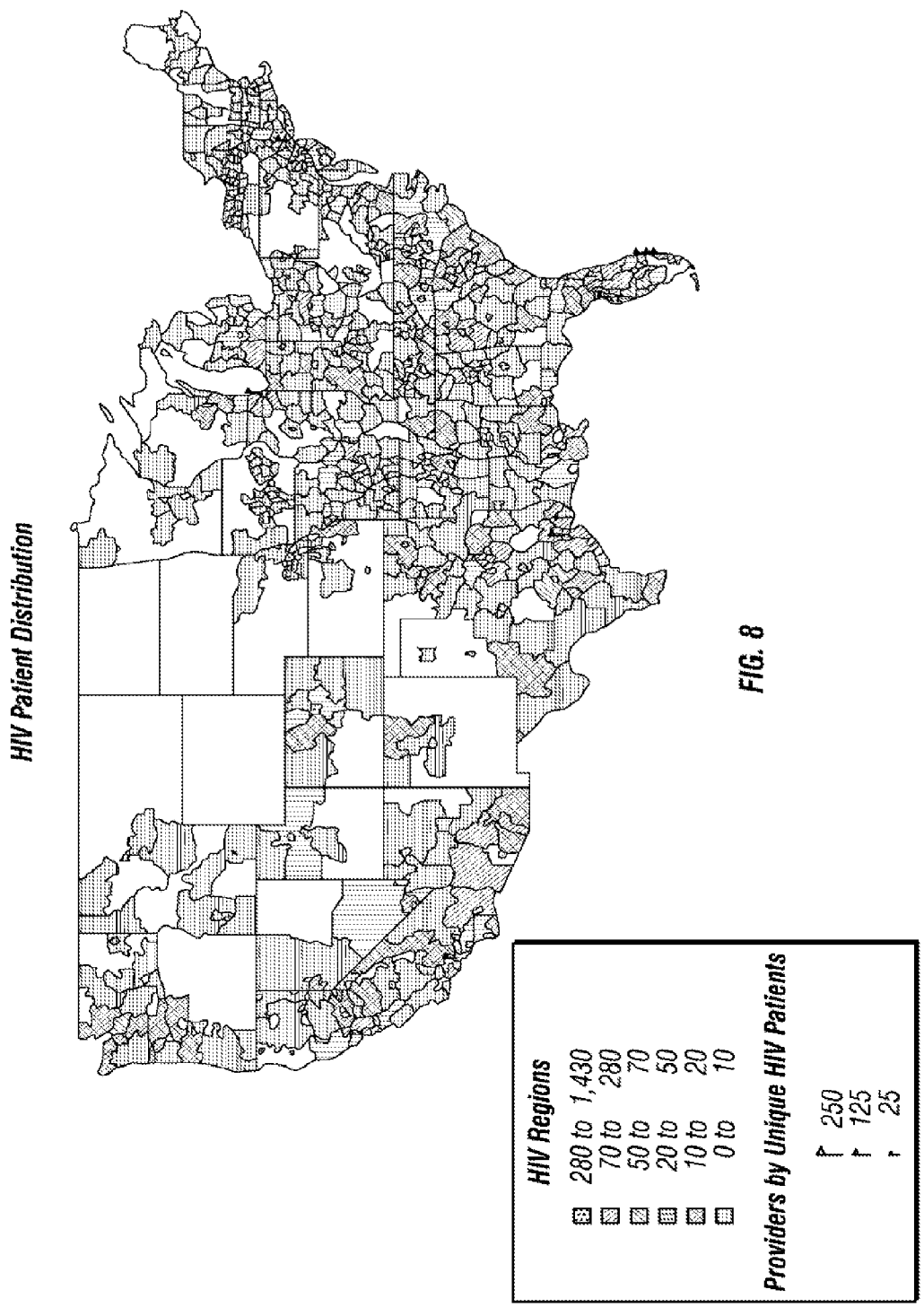
FIGS. 8-9 are map-based customized reports, in accordance with embodiments of the invention.
Figure 9:
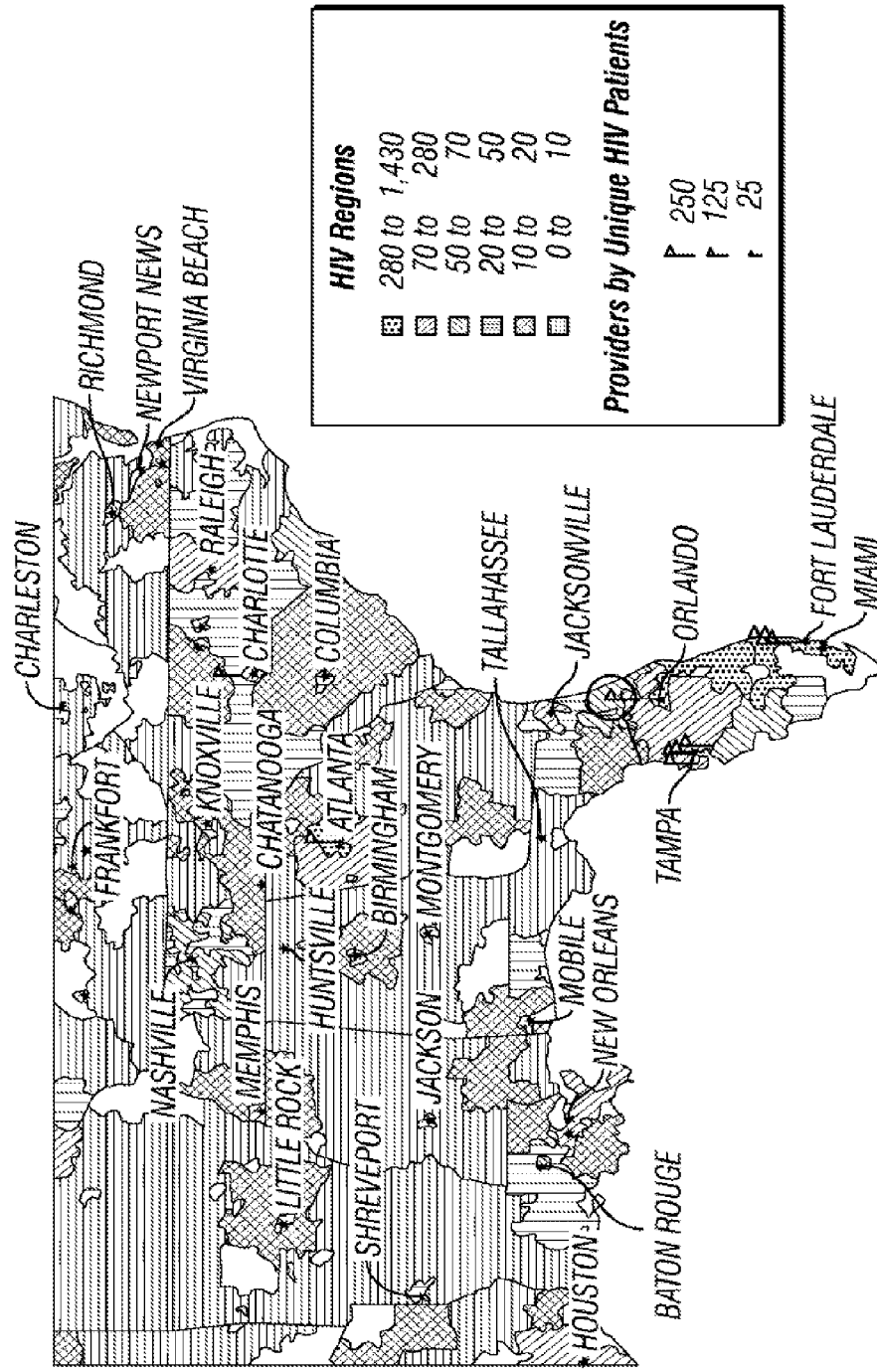

A map-based report takes advantage of geographical information pulled from the underlying data and may advantageously provide a convenient mechanism for a user to quickly determine what area of the country would be a suitable site for a clinical trial, for a job fair, etc. With geographic information accessible, one may study geographic propagation associated with one or more criteria. For example, map based reports may be "put in motion" by employing successive map frames. This may essentially create a "Doppler like" view of the propagation of disease, test subjects, etc. over time. Intensity of the subjects area can be conveyed thematically by color, shading, object size, height, etc. The time period can be aggregated by any desired interval to visibly accent seasonal variations or long term trends. FIGS. 8-9 are examples of map-based, customized reports. In FIG. 8, a United States map is shown, with an HIV patient distribution as an overlay. HIV patient totals are given as a function of region, and information is provided as a function of region for health providers. FIG. 9 is a zoomed-in region of the map of FIG. 8.

Those having ordinary skill in the art will recognize that several other types of customized reports may be generated. In one embodiment, for example, one may generate a customized report that is a provider report. The provider report assists in identifying and enrolling clinical investigators and may be similar to those shown in, e.g., FIGS. 8-9.

It may also be beneficial to link data for clinical trial recruitment applications with data maintained by, e.g., the Center for Disease Control (CDC). This linkage, or other similar linkages, can allow one to calculate different metrics for confirmation of data or for other purposes. For example, by comparing to CDC data, one can determine if the number of hits received for a certain condition in a certain geographical area is "in line" with CDC information for the same condition. If a search indicates that City A has 5,000 adult patients with HIV (out of a total of 400,000 adult patients total for City A residing in the database(s) being searched), a comparison with CDC information regarding HIV rates in City A may serve as a confirmation of the 1.25% HIV rate or an alert if the CDC information indicates a substantially different rate. A confirmation with other data such as CDC data can be indicated on a customized report through a change in color, a confirmation symbol (e.g., a check mark), or the like.

In one embodiment, information pulled to generate a customized report may be linked or compared to information from the U.S. Census to arrive at patient percentage values or the like. For example, if 5,000 adult patients in City A are identified as being associated with HIV diagnoses, and one knows that there are 400,000 adult patients total for City A residing in the database(s) being searched, then one may assume that about 1.25% of City A's adults have an HIV-related diagnosis. If Census data reveals that City A has an adult population of 2.1 million people, one can estimate that there are approximately 2,100,000*0.0125=26,250 adults in City A with HIV-related diagnoses. These types of calculations may be used to effectively normalize data among cities with vastly different populations—i.e., having 200 "hits" in a large city may actually indicate that it would be a more difficult recruiting region than a significantly smaller city having the same number of hits. Using data that shows city size, one may readily arrive at density or other metrics, which would indicate the number of patients per square mile, etc. Of course, such techniques are not limited to the identification of clinical investigators and potential trial subjects. They may be applied to any application discussed here or recognized by those having ordinary skill in the art.

Figure 2:
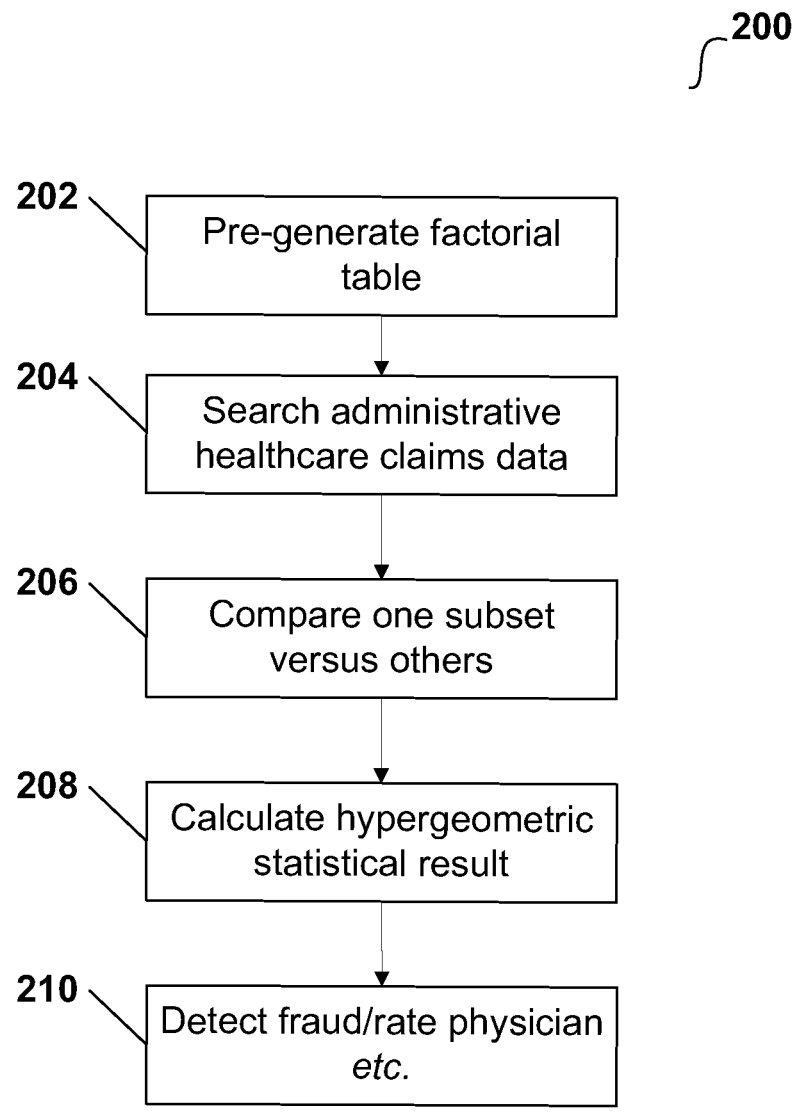
FIG. 2 is a flowchart showing a computerized method for statistical calculations based on administrative healthcare claims data, in accordance with embodiments of the invention. The steps of FIG. 2 can also be used for other applications.

Turning now to FIG. 2, an example method 200 is shown for handling statistical calculations or operations, which can be based on administrative healthcare claims data or other data. In preferred embodiments, the statistical calculations or operations can be used in conjunction with the techniques illustrated in FIG. 1 and described herein.

Pre-Generate Factorial Table

The calculation of certain statistics has historically caused problems. With respect to hypergeometric calculations, there has been a tradeoff between accuracy and speed. In 1993, Wu published an algorithm that addressed a number of performance issues involved in processing, especially in dealing with the large factorial sets needed for hypergeometric calculations. However, while performance using the Wu algorithm may be faster than other conventional techniques, the inventors found it insufficient for, e.g., real time return sets from tens of thousands of attribute/outcome sets requiring full processing. Also, the Wu code requires over/under flow logic when generating an initial recursion point H(0).

The cumulative hypergeometric function can be calculated in a number of different ways. Typically each probability "p" value (pdf) is generated in some fashion and the values are summed to compute the cumulative density function (cdf). For large populations, challenges exist in both the pdf and cdf computations. The pdf calculation can be difficult because large factorials must be processed. Wu tackles this issue by breaking the factorial terms into prime numbers with exponents and reducing each prime/exponent combination to its simplest value. The remaining primes in the numerator and denominator are then processed in such a way that over/under flow issues will not manifest. Once this first probability term, h(0), is calculated, then the other probability terms can be quickly generated and summed to a cdf using known recursion techniques; again with care to avoid over/under flow. Issues arise when many cdfs need to be computed and the factorial→prime sets→cancellation→computation process must be processed, and generate accurate results, many thousands of times. This process has limitations but can be coded directly in SQL (below) to return pdf values. Table ALL59701 contains the prime factorization of every factorial 0 through 59,701.

```
SELECT value,row_number( ) over ( ORDER BY value ASC)
rank_asc,row_number( ) over ( ORDER BY value DESC) rank_desc
    FROM
    (
    SELECT
    (POWER(primenumber,((n1_exp+n2_exp)-(d1_exp+d2_exp))))
        value
FROM
    (
    SELECT primenumber
        ,SUM(CASE WHEN n1=number_of_interest AND
        prime_exp IS NOT NULL
    THEN prime_exp ELSE 0 END) N1_exp
        ,SUM(CASE WHEN n2=number_of_interest AND
        prime_exp IS NOT NULL
    THEN prime_exp ELSE 0 END) N2_exp
        ,SUM(CASE WHEN d1=number_of_interest AND
        prime_exp IS NOT NULL
    THEN prime_exp ELSE 0 END) D1_exp
        ,SUM(CASE WHEN d2=number_of_interest AND
        prime_exp IS NOT NULL
    THEN prime_exp ELSE 0 END) D2_exp
        FROM
        (
        SELECT a.n1,a.n2,a.d1,a.d2,number_of_interest , primenumber,
(prime_exponent) prime_exp FROM (SELECT 866 n1,1591
n2,1745 d1,712 d2 FROM
dual) a,ALL59701iot b
    WHERE a.d1=b.number_of_interest OR
    a.d2=b.number_of_interest OR
a.n1=b.number_of_interest OR a.n2=b.number_of_interest
    ) GROUP BY primenumber
```

-continued

```
) WHERE ((n1_exp+n2_exp)-(d1_exp+d2_exp)) <>0
) ORDER BY rank_asc*rank_desc
```

Table ALL59701 showing the representation of 20000! expressed as a series of prime^exp values:

| NUMBER_OF_INTEREST | PRIMENUMBER | PRIME_EXPONENT |
|---|---|---|
| 20,000 | 2 | 19,995 |
| 20,000 | 3 | 9,996 |
| 20,000 | 5 | 4,999 |
| 20,000 | 7 | 3,332 |
| 20,000 | Many others . . . | Many others . . . |
| 20,000 | 19,991 | 1 |
| 20,000 | 19,993 | 1 |
| 20,000 | 19,997 | 1 |

A faster method that still yields results accurate to 30 decimal places (as tested against published values, e.g., Wu) uses a different form of the factorial table. Instead of expressing factorials as prime^exp pairs, the factorial is expressed as a logarithm (any base). In this case the computation SQL can be written as:

```
SELECT SUM (CASE
            WHEN n1c = number_of_interest
            THEN ln_factorial
            ELSE 0
        END)
```

-continued

```
    + SUM (CASE
            WHEN n2c = number_of_interest
            THEN ln_factorial
            ELSE 0
        END)
    - SUM (CASE
            WHEN d1c = number_of_interest
            THEN ln_factorial
            ELSE 0
        END)
    - SUM (CASE
            WHEN d2c = number_of_interest
            THEN ln_factorial
            ELSE 0
        END) VALUE
    INTO h_accum
    FROM (SELECT /*+ index(b)*/
                n1 n1c, n2 n2c, d1 d1c, d2 d2c, number_of_interest,
                ln_factorial
        FROM ALL_10M b
        WHERE d1 = b.number_of_interest
            OR d2 = b.number_of_interest
            OR n1 = b.number_of_interest
            OR n2 = b.number_of_interest)
GROUP BY n1c, n2c, d1c, d2c;
```

Where the table ALL_10M contains the log value of all factorials 0 through 10,000,000:

| NUMBER_OF_INTEREST | LN_FACTORIAL |
|---|---|
| 20000 | 178075.6217371987003128679281773311631722 |

As a check on the internal representation on the values one can see for this computation of large factorials the value differs from 20001 only in the 31st decimal place. Steps may also be taken to represent logarithmic values in the best possible datatype/format for a given platform.

```
SELECT EXP(a.LN_FACTORIAL-B.LN_FACTORIAL)||''
        factorial_check
FROM
    (SELECT a.NUMBER_OF_INTEREST,a.LN_FACTORIAL
        ln_factorial FROM
ALL_10M a WHERE a.NUMBER_OF_INTEREST=20001)a,
    (SELECT a.NUMBER_OF_INTEREST,a.LN_FACTORIAL
        ln_factorial FROM
ALL_10M a WHERE a.NUMBER_OF_INTEREST=20000) b
FACTORIAL_CHECK
20000.9999999999999999999999999999999855
```

In one embodiment, The table ALL_10M may be created and populated in the following manner

```
CREATE TABLE ALL_10M
(
NUMBER_OF_INTEREST  NUMBER        NOT NULL,
LN_FACTORIAL        NUMBER        NOT NULL,
CONSTRAINT PK_ALL_10M
PRIMARY KEY
(NUMBER_OF_INTEREST)
)
ORGANIZATION INDEX
NOLOGGING; ,
``` and then running a script as below. This may take less than 1 hour on a modest platform to complete.

```
CREATE OR REPLACE PROCEDURE Factorial10
IS
    -- fills all_10M table with pairs of: number, LN(number!)
        i                               NUMBER;
        last_i                          NUMBER;
BEGIN
        INSERT INTO ALL_10M
            VALUES (0, 0); -- 0!=1 and LN(1)=0
        last_i := LN (1);
        FOR i IN 1 .. 10000000
        LOOP
            INSERT INTO ALL_10M
                VALUES (i, LN (i) + (last_i));
            last_i := LN (i) + last_i;
            IF i/100000=ROUND(i/100000) THEN -- commit every
            100K
                COMMIT;
                dbms_output.put_line( i );
            END IF;
        END LOOP;
        COMMIT;
END Factorial10;
/
```

Hypergeometric calculations have a wide range of uses. One such use pertains to the generation of probability scores for drug safety measurements. Consider that two populations are very similar except that one group has taken drug "A" and the other group has taken drug "B" (or a placebo, or no drug at all). At the initiation of each drug the index_date is defined. The index date is the beginning of the "outcome" period. Typically, a patient is exposed to a new drug, procedure, diagnosis, event, etc. on the index date. This new condition could be as varied as "stopped smoking," "received coronary bypass surgery," "began taking drug X," "was diagnosed with a hernia," "began working at a particular location or job," "began seeing a particular physician," or any other event, medical or non-medical. The index date for each individual in both population set is then normalized to zero. Prior to the index date each member has a set of attributes including but not limited to, gender, age, region, diagnosis, procedure, drug codes, etc. After the initiation of the drugs all following codes are tagged as emergent. These emergent conditions may or may not be related to the index drugs. If the two populations are well matched, one can surmise that adverse drug effects related to, say, drug A, will be more prevalent in the drug A population immediately or after prolonged exposure to drug A. Certain subgroups and even "sub-sub" groups may be especially susceptible to these adverse effects. For instance women may be more susceptible to, say, dizziness when taking drug "A" than men taking drug "A".

| Cluster | Population | Condition | Signal Drug A | Signal Drug B |
|---|---|---|---|---|
| ALL | ALL | Dizziness | weak | none |
| Sub group | Women | Dizziness | moderate | none |
| Sub-sub group | Women on Thyroid drugs | Dizziness | strong | none |

It should be noted that an adverse signal could be actually reflecting the suppression of an outcome by the other comparing drug. (e.g., if drug B happens to cure dizziness in women on thyroid drugs and drug A neither causes or suppresses dizziness then drug A could show a "dizziness" signal even though the symptom was no higher than the rate in women taking thyroid medication in the general population).

Using such techniques and those of the rest of this disclosure, one may be capable of, among other things, rapidly:
  a. Creating attribute clusters;
  b. Creating outcome clusters;
  c. Scoring all permutations of attribute/outcome clusters (i.e. finding the sub groups with the strongest signals for each emergent condition); and
  d. Presenting only the most significant permutations.

In one embodiment, a solution to problems associated with prior algorithms is, in general, two-fold: (1) eliminate the expensive initial factorial operation associated with hypergeometric calculations by using a table containing pre-generated factorials (e.g., caching the natural log (LN) or LOG 10 value (or other differently-based log value) of each factorial), and (2) code the recursion for the H(x) integration entirely in logarithms until a final cumulative P value is computed.

In step 202 of FIG. 2, one or more factorial tables are pre-generated. In a preferred embodiment, these specialized tables allow for the calculation of hypergeometric statistical results, and they ensure that such calculation proceeds swiftly. The factorial tables may be similar to look-up tables, in which the logarithm of different factorial numbers are listed for quick access. As explained more below, after calculations or other operations are performed using the logarithms, an exponential can be taken.

Search Administrative Healthcare Claims Data

In step 204 of FIG. 2, administrative healthcare claims data is searched. In other embodiments, different types of data may be searched using the same techniques. In fact, any searchable repository of data (e.g., database) may benefit from this disclosure, and particularly data for which hypergeometric statistical results are desired. The actual execution of the search in step 204 depends upon what statistical result or analysis the user is seeking to generate. But, in a preferred embodiment, the search step 204 entails the searching of records so that one subset can be compared against another, as detailed below.

In one embodiment, search step 204 may entail the searching of one or more SSTs, as detailed above and herein. For example, search step 204 may encompass the searching of one or more SSTs alone or in combination with the searching of raw data from one or more databases. In the situation in which SSTs are being searched, the user may see even greater speed and efficiency.

Comparing One Subset Versus Others

In step 206 of FIG. 2, one subset of administrative healthcare claims data is compared against other subsets of the administrative healthcare claims data in order to arrive at a statistical result (see discussion below for embodiments in which the statistical result is based on a hypergeometric calculation). In a preferred embodiment, information associated with one patient or physician is compared against information associated with all other patients or physicians. The first subset may be a single record or group of records associated with an individual, while the other subset may be a million or more records associated with other individuals. In other embodiments, the record or records associated with an individual can be compared against the records of those who have something in common with the individual—for example, the records of one physician can be compared against records of other physicians practicing in the same medical specialty. Or, the record or records of an individual can be compared against the records of other patients who suffer from the same or similar medical condition. Those having ordinary skill in the art will recognize that the selection of different searching subsets can be chosen at will, and according to desire, in accord with the type of statistical result being sought.

Calculating Hypergeometric Statistical Result

In step 208 of FIG. 2, a hypergeometric statistical result is calculated based on the comparing step 206, and using the one or more pre-generated factorial tables of step 202.

To detect fraudulent coding patterns, discussed more below, one may compare the medical coding of an individual doctor against the coding patterns of all other doctors in that specialty, and all the doctors in the top three specialties that have billed against the same diagnostic code. The current state of the art hypergeometric method for doing this analysis against approximately ten million lives would require approximately 100 hours to execute on modern database hardware. As a result, this sort of comprehensive fraud detection would be limited to specific physicians that are suspect of fraudulent behavior.

Using pre-generated factorial tables and the other innovations of this disclosure, however, (1) eliminates the expensive initial factorial operation by using a table containing pre-generated factorials (e.g., caching the LOG 10 value of each factorial) and, (2) coding the recursion for the hypergeometric values entirely in logarithms until a final cumulative value is computed. This process reduces the calculation time for the same fraud screen against approximation ten million lives to approximately six minutes (a speed increase of about 1000 times). As a result, a fraud screen can be continuously run against a much larger number of doctors, and new hypothesis for fraud detection can be developed much more quickly (e.g., six minutes to see if there is a useful signal, instead of 100 hours). With this type of speed, one can apply different "what if" tests to extremely large data sets and get answers in minutes and hours, not weeks and months.

Computationally expensive processes in the hypergeometric calculations have been recoded by the inventors using factorial lookups and natural logarithms to yield accurate P values in milliseconds. As specified by Wu (shown here in the two equation sets immediately below) and others, a specific pdf can be obtained by direct calculation of factorials. Below, N is the total population, n is a subgroup of the population, r is the sample set taken form the population without replacement, and x is the number of "hits" in the sample set.

$$h(x; r, n, N) = \frac{n!r!(N-n)!(N-r)!}{N!x!(n-x)!(r-x)!(N-n-r+x)!},$$

where $\max(0, r-N+n) \leq x \leq \min(r, n)$.

Or, for the simple case when x=0

$$h(0; r, n, N) = \frac{m(m-1)\ldots(m-r+1)}{N(N-1)\ldots(N-r+1)}$$
$$= \frac{m!(N-r)!}{N!(m-r)!},$$

where $m = N - n$.

Prior to recursion, if the starting pdf value (initial recursion point) is not zero because, e.g.:

1. Summing the smaller tail would be faster or
2. Zero is an undefined starting point, then, for these special cases, one may use the longer form:

```
SELECT SUM (CASE
            WHEN n1c = number_of_interest
            THEN ln_factorial
            ELSE 0
        END)
     + SUM (CASE
            WHEN n2c = number_of_interest
            THEN ln_factorial
            ELSE 0
        END)
            + SUM (CASE
                WHEN n3c = number_of_interest
                THEN ln_factorial
                ELSE 0
            END)
            + SUM (CASE
                WHEN n4c = number_of_interest
                THEN ln_factorial
                ELSE 0
            END)
     - SUM (CASE
            WHEN d1c = number_of_interest
            THEN ln_factorial
            ELSE 0
        END)
     - SUM (CASE
            WHEN d2c = number_of_interest
            THEN ln_factorial
            ELSE 0
        END)
            - SUM (CASE
                WHEN d3c = number_of_interest
                THEN ln_factorial
                ELSE 0
            END)
            - SUM (CASE
                WHEN d4c = number_of_interest
                THEN ln_factorial
                ELSE 0
            END)
            - SUM (CASE
                WHEN d5c = number_of_interest
                THEN ln_factorial
                ELSE 0
            END) VALUE
    INTO h_accum
    FROM (SELECT /*+ index(b)*/
            n1 n1c, n2 n2c, n3 n3c, n4 n4c, d1 d1c, d2 d2c,d3 d3c, d4
            d4c,d5 d5c,
number_of_interest,
            ln_factorial
        FROM ALL_10M B
        WHERE d1 = B.number_of_interest
        OR d2 = B.number_of_interest
            OR d3 = B.number_of_interest
            OR d4 = B.number_of_interest
            OR d5 = B.number_of_interest
        OR n1 = B.number_of_interest
        OR n2 = B.number_of_interest
            OR n3 = B.number_of_interest
        OR n4 = B.number_of_interest);
    h_sum := EXP (h_accum);
    h_all := h_accum;
    tail_integration_pt:=1 for typical h(0) starts;
    or tail_integration_pt:=(n-(ntot-r))+1 <for starting at first defined
    point>;
```

Once the ln(pdf) is processed, shown here as h_accum, it can be directly converted via exp(h_accum), shown as h_sum. This pdf can then be used to recursively generate the additional terms in one of two ways. If one wishes to avoid over/under flow issues at the expense of a modest performance hit, the recursion steps can be processed in logarithms.

```
FOR i IN tail_integration_pt .. k
    LOOP
        x := i - 1;
```

-continued

```
    h_all :=
        h_all + LN ( ( n - x )
            * ( r - x )
            / ( x + 1 )
            / ( ntot - n - r + x + 1 ));
    h_sum := h_sum + EXP (h_all);
END LOOP;
RETURN h_sum;
```

Alternately, one can recursively process in natural numbers after the exp conversion taking care to avoid over/underflow.

```
FOR i IN tail_integration_pt .. k
LOOP
    x := i - 1;
    h_all :=
        h_all * ( ( n - x )
            * ( r - x )
            / ( x + 1 )
            / ( ntot - n - r + x + 1 ));
    h_sum := h_sum + (h_all);
END LOOP;
RETURN h_sum;
```

Yet another possibility is to repeatedly call the master SQL and "exp" and then sum each h(x) term one by one.

Hypergeometric processing has applications in quality control, pattern recognition, cluster validity analysis, tree classifier design, image template matching and other areas.

Techniques of this disclosure allow one to apply statistical methodology to large data sets or dynamic data feeds for real-time consideration of data population statistical characteristics. Table structures may be optimized such that blocks (e.g., ORACLE blocks) are "rich" in the desired filter criteria. This enables access of hundreds of thousands of lines of data in a few seconds. One can thus quickly find data of interest, cluster it into appropriate groupings, apply hypergeometric processing to the data sets, and present only the "interesting" cases, as determined by their hypergeometric score, to a user or other.

Detect Fraud, Rate Physicians, and Other Applications

In step 210 of FIG. 2, one uses the hypergeometric statistical result to draw some conclusion from the administrative healthcare claims data. In one embodiment, the steps of FIG. 2 may be used to determine whether one or more physicians may be involved with medical fraud. In such an embodiment, the search and comparison steps 204 and 206 may involve comparing billing practices (e.g., CPT or other medical codes) associated with the physician against the billing practices of other groups of physicians (e.g., against other groups in total, against groups having the same medical specialty, against groups sharing the same geographic region, against groups of similar age, etc.). In one embodiment, results of the fraud investigation can be output to form a customized report.

In the medical field, fraud detection is an area of interest. Opportunistic behavior by medical staff can manifest in unlikely proportions of lucrative procedures being performed. Rather than merely stating Dr. X performs procedure Y a certain percentage (e.g., 30%) more often than his or her peers, one can compute based on the total population of patients requiring procedure Y, the likelihood that Dr. X would have a certain number of patients (e.g., 30) requiring the procedure. If the likelihood is greater than a certain amount (e.g., 1 in 10,000,000 or other value defined by a user or other entity), action can be taken to look more closely at the case. This can be extended to any pairings of medical codes. For example, this may be extended to scenarios such as:

hospital A dispensed a narcotic for diagnosis B seventy times for its 120 patients with diagnosis B. Nationally, 270 patients were treated in hospitals this way out of 3400 with diagnosis B. How likely is this scenario?

This is one example only with example figures. Those of ordinary skill in the art will recognize other applications using these same or equivalent techniques. Many factors may need to be taken into account before action would be warranted with respect to fraud enforcement. Techniques of this disclosure, however, can quickly generate a working list sorted by least to most likely events to assist in the fraud detection/enforcement process. For disease clustering, one can call the hypergeometric to calculate the likelihood that X cases of disease Y would occur in a particular geographic region in a given interval knowing Z cases occurred nationally in that interval. Again, various other applications will be apparent to those having ordinary skill in the art.

Figure 10:
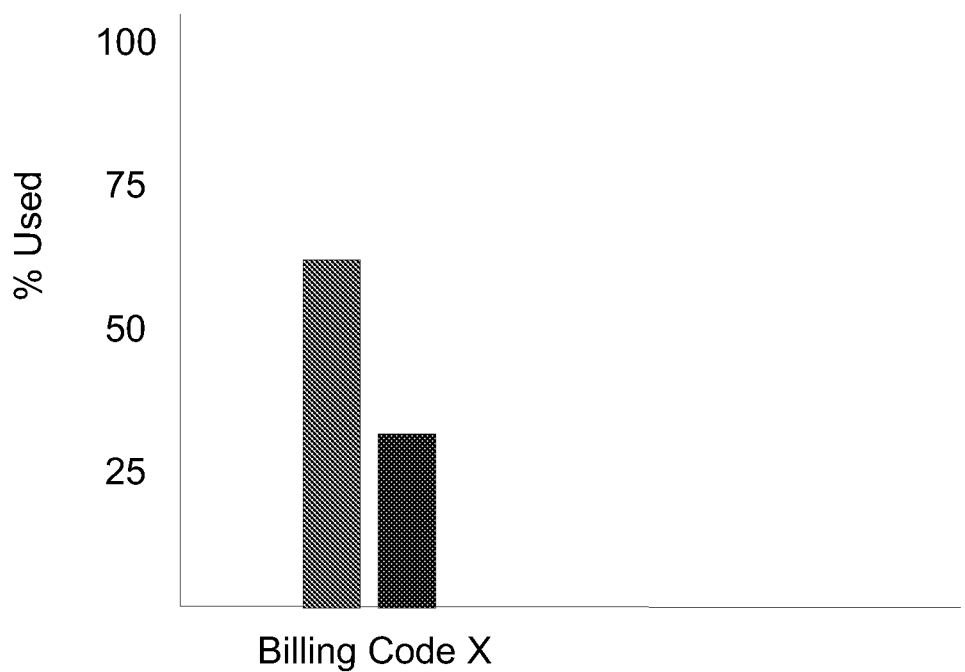
FIG. 10 is a customized report directed at fraud detection, in accordance with embodiments of the invention.

An example customized report may constitute a graph of utilization percentage versus medical billing code for a first physician versus a group of other physicians (e.g., others in his or her specialty). An example graph is shown in FIG. 10. There, the red bar (left) represents a physician under investigation. The blue bar (right) represents thousands of other physicians practicing in the same specialty. The data reveals that the physician under investigation utilizes billing code X significantly more than his or her peers. This may signify fraud.

Comparing one subset of individuals versus another and searching for resulting patterns, especially in conjunction with hypergeometric calculations, can be applied to many other applications other than medical fraud detection. In one embodiment, one may use the comparisons and other steps like those in FIG. 2 to rate or score physicians. Any comparison in view of a peer group can constitute a score. For physician quality scoring, one might measure patient wellness (according to one or more of many methods known in the art) across various ETG groupings and determine a physician's quality of care measure against peers treating individuals in similar ETG groups. This could be extended to look for unconventional treatment patterns that yield beneficial results even though they may not conform to existing "best practices". This may or may not be a drug related effect, or may involve combination of drugs and procedures. For example, one may generate statistics such as: of the W people with chronic condition "A" who had a typically unrelated procedure "B", X showed improvement as measured by lab results OC1, hospital stay length OC2, or other wellness indication. Of the total population of Y people with chronic condition "A" who had similar treatments except for procedure "B", Z showed improvement. Such statistics may point to beneficial results, correlations, may suggest research avenues, etc.

In another embodiment, the comparisons may be used for marketing. One may run comparisons of physicians based on geographical area to determine if there are any patterns concerning drugs being prescribed. If it is found that one region lags behind, marketers may want to focus on that region to bring its statistics in line with other regions. One may run comparisons of physicians based on where they went to medical school to determine if there is a correlation between medical school and drugs being prescribed. Marketers may then want to focus efforts on some schools more than others. Those of ordinary skill in the art, with the benefit of this disclosure, will recognize many other similar marketing applications.

In another embodiment, the comparisons may be used for drug safety studies. The i3 APERIO DRUG REGISTRY product from Ingenix, Inc. can be used for such purposes. By looking at the relevant intersection points of thousands, millions, or billions of data elements, one may answer the question, "Is drug A safer to use than drug B?." Specifically, the use of a real-time hypergeometric calculation allows one to place billions of data points into their respective numerator/denominator positions and to identify the most meaningful data intersections needed to answer the question. It is believed that this will open up new signal detection opportunities in at least the drug safety and fraud detection arenas. Combining the innovations with hypergeometric calculations described here with the SST innovations, one may quickly integrate hypergeometric functions with extremely large data sets and scale to even larger data sets, while minimally reducing speed.

SSTs Used in Combination with Hypergeometric Factorial Tables

In different embodiments, both SSTs and factorial tables having logarithmic entries for improved hypergeometric calculations can be used together to provide even more robust data mining and analysis. For example, the hypergeometric may be used to find disease hot spots and physician hot spots. Additionally, both SSTs and factorial tables may be used in conjunction with the identification of potential subjects for clinical trials. Using both SSTs and factorial tables, clinical research organizations are given the ability to pinpoint a population substrate and identify clinical investigators for drug trials to answer questions such as, "What is the context of the disease in the U.S. and which sites should be selected for conduct of the study based on disease prevalence?"

Both SSTs and factorial tables can also be applied to applications in which a medical expert witness (or other professional) is being recruited. For example, attorneys and law firms are provided the ability to answer questions such as, "Who can provide medical expert testimony in a case involving medical conditions A, B and C?"

Use of Technology for Modeling

Because one can so quickly mine and analyze massive amounts of administrative healthcare claims data, the techniques of this disclosure allow users to model clinical trials or other application in real-time or near-real-time. For example, individual iterations of modeling may occur approximately once per 10 minutes in one embodiment, once per 5 minutes in another embodiment, once per 2 minutes in another embodiment, once per 1 minute in another embodiment, once per 30 seconds in another embodiment, once per 10 seconds in another embodiment, once per 5 seconds in another embodiment, once per 2 seconds in another embodiment, once per second in another embodiment, once per ½ second in another embodiment, once per ¼ second in another embodiment, and so on. Using clinical trials as an example, one may define exclusion or inclusion criteria, run a search, determine a potential subject pool, and model how that population pool would change by modifying the exclusion or inclusion criteria. In a preferred embodiment, the user compares the potential subject pool returned by a search against a minimum subject participation—a quantitative measure (e.g., total subjects, subject density, etc.). If the potential subject pool is less than the minimum subject participation, the user may modify the exclusion or inclusion criteria until the minimum subject participation is met or exceeded.

In one embodiment, the exclusion or inclusion criteria may be modified automatically until a target subject participation value is at least met or exceeded (or, in other embodiments, until the potential patient pool is less than a given target). The automatic modifications to the exclusion or inclusion criteria may be done within pre-defined ranges set up by the user, according to different priorities assigned by the user, or through other means to ensure that the modified exclusion or inclusion criteria still define a useful criteria for the study. Neural network technology or other computer science principles known in the art may be employed in this modeling process. In embodiments using automatic modifications, the modifications may be done iteratively until a target is met. If the exclusion or inclusion criteria do not meet the target after a pre-determined number of iterations or time period an error or alert may be generated.

Use of Technology for Additional Applications

The numbered list below summarizes some applications already discussed here and includes others that may be readily adapted using the description above. The applications listed below may make use of, e.g., SSTs and/or factorial tables for searching and statistical calculations, respectively. The applications may track the steps in FIG. 1 or 2. For example, following FIG. 1, searching criteria may be defined, followed by pre-generation of SSTs, followed by a search, followed by the identification of pertinent "hits," followed by the generation of a customized report presenting or summarizing information about the "hits" in a user-convenient format, such as by geography. Likewise for statistical calculations, and following FIG. 2, the applications listed below may pre-generate one or more factorial tables, search data, compare one subset of data versus others, calculate a statistic using the factorial tables, and then reach (or assist the user in reaching or postulating) a conclusion based on the statistic that was calculated.

Those having ordinary skill in the art will recognize that there are many other applications, and those mentioned here are not meant to be an exhaustive list.

1. Clinical trial investigator and potential trial subject identification. Researchers are able to identify potential clinical investigators and subject pools quickly. Geographical or other types of reports may be generated. Due to speed, clinical trials can be modeled to arrive at exclusion or inclusion criteria suitable for enrolling investigators and recruiting an adequate number of subjects in advance of first participant's, first visit. This application can save millions of dollars by avoiding delay during the recruitment phase of a trial.

2. Recruitment of medical directors and expert medical witnesses. Lawyers, legal assistants, hospital and physician recruiting firms, or other users are able to quickly determine where a suitable medical directors and medical expert witnesses may be found or, more directly, who might be a good fit for a particular position or case. Searching parameters may be chosen to ensure that the expert will have the appropriate experience or attributes being sought by the recruiting firm or legal team. Due to speed, modeling may be done—the user can model the number or type of experts depending on changes in searching parameters.

3. Analysis of medical litigation. Through the improved data mining and analysis techniques described here (e.g., use of SSTs and/or factorial tables), lawyers or other users may assess the validity or likelihood of success of a medical litigation. For example, one may analyze a historic claims profile to identify treatment profiles of subjects similar to a client to determine, e.g., other maladies suffered by such individuals. By comparing the client's treatments against hundreds, thousands, or millions of similarly-situated treatment patterns, the legal team may discover "holes" in their case or opportunities for additional arguments/theories.

4. Counseling of medical school students. By mining and analyzing claims data, one may present to medical school students (or others) an overview of the type of diseases that, on average, are being seen by specific specialties. Such information may be useful to various specialty colleges for recruitment.

5. Ancillary Product Marketing. Through analysis of claims data or other data, one may correlate, e.g., use of a particular drug with other buying habits (e.g., if a person uses drug A, it appears he or she may also use drug/product X, Y, or Z). This information may be used in marketing. For example, marketers may use the correlations for online advertising—along with links related to drug A, it may be useful to display banner ads for drug/product X, Y, or Z.

6. Job Placement. One may find suitable job candidates for a variety of different jobs using the techniques described here. For example, pharmaceutical companies may search for a candidate having particular experience as a physician prescribing a certain category of drugs, or investigating certain illnesses.

7. Continuing Medical Education (CME). Techniques of this disclosure may allow CME companies the ability to "measure" practice patterns before and after a CME program.

8. Marketing. Techniques of this disclosure may allow marketers the ability to "measure" how effective an ad campaign was. For example, if millions of dollars were spent in city X promoting drug Y, one could monitor over a period of time whether the prescribing habits of physicians changed with respect to drug Y in city X. One can monitor for changes in physician treatments, drug penetration, sales volume, growth trends, etc.

9. Regulatory application. Regulatory agencies charged with the responsibility of clinical trial oversight (e.g., FDA in the US, EMEA in the European Union) would be able to modify requirements for registrational trials based on feasibility evidence as well as evaluate how compliant to marketing approval particular drugs are with reports generated from techniques of this disclosure. Agencies such as the CDC or WHO would be able to implement real time surveillance programs of drug resistance and emerging pathogens from techniques of this disclosure.

10. Physician Scorecard. By comparing one physician versus others in virtually any category supported by underlying data, a scorecard system can be created. This, for example, may provide a comparative analysis for each physician of coding practices relative to a chosen benchmark (could be billing, outcomes, script usage, etc.). An "alerting" system may be included to trigger an alarm if threshold values are exceeded.

11. PharmaSolutions. Through quick analysis of claims data, one may characterize key issues for a drug prior and after market launch—(1) compliance with regimen compared to others in-class meds, (2) usage of drugs by indication that would provide insight into marketing needs, (3) prescribing habits of particular drugs or drug classes based on physician profiling (e.g., demographics or training institution)]., or (4) evaluation of drug utilization based on demographics or other available claims variables for market characterization.

12. Consumer Preventive Health Solutions. Through analysis of claims data as taught here, a health consumer could effectively "see" his or her future. For example, a person could enter his or her current demographic and disease characteristics and then "see" 5, 10, 15, and 20 years into the future by looking at similar consumers in that age group and look at what types of claims are being captured. Conversely, a health system may want to know what a particular consumer may face in terms of claims in the future. Decisions about such consumers as enrollees can then be made.

13. PhysicianClustering. In another marketing-related, application, one may cluster physicians by age, demographics, place of training and determine if there are marketing holes in their prescribing patterns. Or, one may be alerted to poor training that is responsible for illogical prescribing patterns.

14. HealthConsumer. Through analysis of claims data, one may find the "best fit" physician for a particular patient. Health consumers would be able to evaluate, in real time, which physician best met their need with respect to (1) geographic location, (2) mix of patient population, (3) quality measure, and (4) outcomes for patient with similar disease profiles.

15. Serendipitous Reporting System (SRS): One may use hypergeometrics and SSTs to compare claims of subjects and retrospectively determine which interventions (procedure or drug) may have had a positive influence on their disease.

16. Disease Surveillance System Network (DSSN): One may use hypergeometrics and SSTs to identify in real time potential outbreaks of disease that would be considered statistically unlikely to be in accord with background rates.

Hardware

Figure 3:
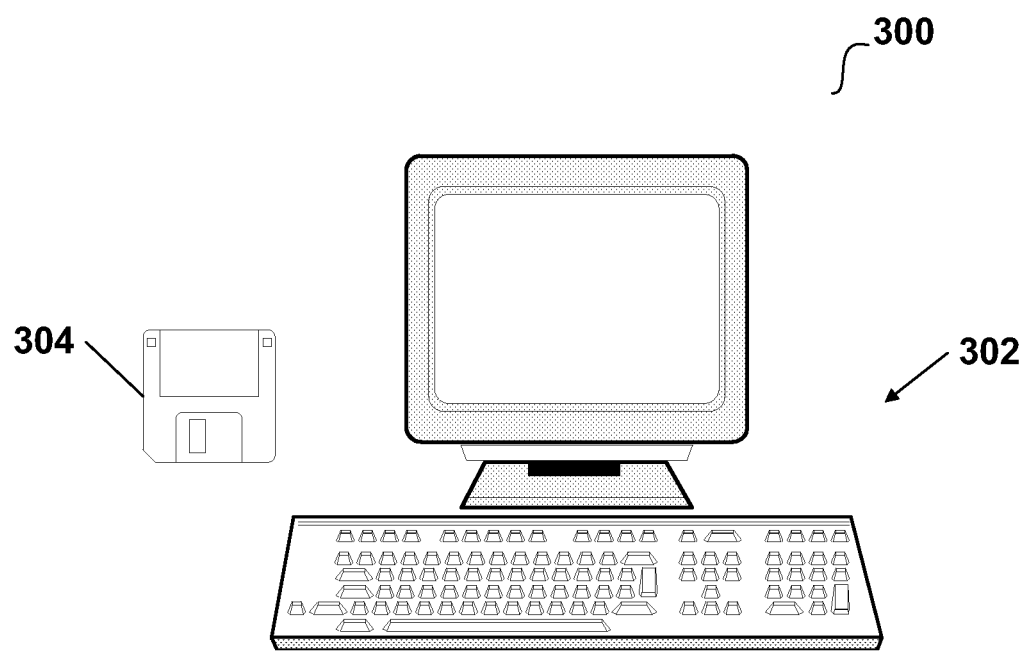
FIG. 3 is a schematic diagram of a computer system including a computer readable medium suitable for carrying out techniques of this disclosure, in accordance with embodiments of the invention.

Turning now to FIG. 3, a schematic diagram of a computer system 300, including computer 302 is shown. Computer readable medium 304, which is here shown as a disk as an example, can be used to house software suitable for carrying out certain techniques of this disclosure. The software may be written using any of a number of programming languages. Suitable languages include, but are not limited to, BASIC, FORTRAN, PASCAL, C, C++, C#, JAVA, HTML, XML, PERL, SQL, db internal languages (e.g., PL/SQL), etc. In one embodiment, commercially available software running one or more scripts or routines can be used for carrying out the invention. For example, one may use MICROSOFT EXCEL or another spreadsheet with appropriate database and analysis functionality to carry out the invention. One may use MATLAB or other mathematical packages for carrying out the invention as well. One may use commercial database software, scripting routines, and the like.

Computer readable medium 304 may be any medium available and which is suitable for storage and which allows for the eventual execution of code by a computing device. Code may be housed on a computer file, a software package, a hard drive, a FLASH device, a floppy disk, a tape, a CD-ROM, a DVD, a network drive, a hole-punched card, an instrument, an ASIC, firmware, a "plug-in" for other software, web-based applications, RAM, ROM, etc.

Computer 302 may be any computing device including but not limited to a personal computer (e.g., a desktop, laptop, tablet, pen, or other computer operated by a user), a personal digital assistant (PDA), or other devices.

In some embodiments, the computer-readable media 304 and computer 302 may be networked. One may use a terminal device running software from a remote server, wired or wirelessly. Input from a user or other coupled system components may be gathered through one or more known techniques such as a keyboard or mouse. Output, if desired, may be achieved through one or more known techniques such as an output file, printer, facsimile, e-mail, web-posting, or the like. Storage may be achieved internally or externally. Any integral or remote display type may be used including but not limited to a cathode ray tube (CRT) or liquid crystal display (LCD). One or more display panels may also constitute a display. In other embodiments, a traditional display may not be required, and the computer-readable media may operate through appropriate voice and/or key commands.

The following examples are included to demonstrate specific embodiments of this disclosure. It should be appreciated by those of ordinary skill in the art that the techniques disclosed in the examples that follow represent techniques disclosed by the inventors to function well in the practice of the invention, and thus can be considered to constitute specific modes for its practice. However, those of ordinary skill in the art should, in light of the present disclosure, appreciate that many changes can be made in the specific embodiments which are disclosed and still obtain a like or similar result without departing from the spirit and scope of the invention.

Example 1

The code below is directed to one example embodiment and includes background information on the pre-generated tables used in the data mining algorithm.

Pre-Generated Tables with Drug Pair, Version Partitions

The following four tables are pre-populated and partitioned by drug pair and version.

CLUSTER_BASELINE_POPS

This table contains all possible attributes for each study participant.

```
CREATE TABLE CLUSTER_BASELINE_POPS
(
    PRODUCT_ID       NUMBER              NOT NULL,
    VERSION_ID       NUMBER              NOT NULL,
    NEWINDV_ID       VARCHAR2(17 BYTE)   NOT NULL,
    GROUPFLAG        NUMBER(1)           NOT NULL,
    ATTRIBUTE        VARCHAR2(30 BYTE),
    ATTRIBUTE_VALUE  VARCHAR2(64 BYTE)
)
```

Where product_id, and version_id are partitioning information

Newindv_id is a unique patient identifier

Groupfalg indicates the population set

Attribute and attribute value generalize all possible attributes, e.g.: newindiv_id 1723423_2 might have:

| Attribute | Attribute Value |
|---|---|
| Gender | Male |
| Dx_code | 410 |
| Region | South |
| Px_code | 87010 |
| Age | 27 |

CLUSTER_XD_XC_PREJOIN_DX_OP

This table contains all possible attribute/outcome pairings for Dx outcome-outpatient events for each study participant.

```
CREATE TABLE CLUSTER_XD_XC_PREJOIN_DX_OP
(
    PRODUCT_ID       NUMBER              NOT NULL,
    VERSION_ID       NUMBER              NOT NULL,
    NEWINDV_ID       VARCHAR2(17 BYTE)   NOT NULL,
    GROUPFLAG        NUMBER(1)           NOT NULL,
    ATTRIBUTE        VARCHAR2(30 BYTE),
    ATTRIBUTE_VALUE  VARCHAR2(64 BYTE),
    OUTCOME_CLASS    VARCHAR2(22 BYTE),
    OUTCOME_TYPE     VARCHAR2(4 BYTE),
    DAYS_IN_STUDY    NUMBER
)
```

Where outcome_class and outcome_type are generic fields for any outcome and days_in_study indicates when the outcome occurred as measured from the index_date, e.g.:

| Outcome_class | Outcome_type | days_in_study |
|---|---|---|
| DX_OUTPATIENT | 337 | 103, | where outcome type 337 might be "Disorders of the autonomic nervous system," or other information.

CLUSTER_XD_XC_PREJOIN_DX_IP

This table contains all possible attribute/outcome pairings for Dx outcome-inpatient events for each study participant.

CLUSTER_XD_XC_PREJOIN_RX

This table contains all possible attribute/outcome pairings for Rx outcome events for each study participant.

The CLUSTER_XD_CD_PREJOIN_{value} tables, such as the two mentioned above, may be of the following example form:

```
CREATE TABLE CLUSTER_XD_XC_PREJOIN_????
(
    PRODUCT_ID       NUMBER              NOT NULL,
    VERSION_ID       NUMBER              NOT NULL,
    NEWINDV_ID       VARCHAR2(17 BYTE)   NOT NULL,
    GROUPFLAG        NUMBER(1)           NOT NULL,
    ATTRIBUTE        VARCHAR2(30 BYTE),
    ATTRIBUTE_VALUE  VARCHAR2(64 BYTE),
    OUTCOME_CLASS    VARCHAR2(22 BYTE),
    OUTCOME_TYPE     VARCHAR2(4 BYTE),
    DAYS_IN_STUDY    NUMBER
)
TABLESPACE USERS
PCTUSED 0
PCTFREE 10
INITRANS 1
MAXTRANS 255
PARTITION BY RANGE (PRODUCT_ID, VERSION_ID)
( partition terms)
```

Pre-generated tables not related to drug pairs

Additionally a couple other pre-generated tables are used.

```
ALL_CODE_XWALK
Contains Dx/Px/Rx code descriptions
CREATE TABLE ALL_CODE_XWALK
(
    CODE_TYPE CHAR(2 BYTE),
    CODE_SET VARCHAR2(8 BYTE),
    CODE_DESC VARCHAR2(220 BYTE)
)
```

Where code_type is PX,RX or DX, Code_set is the actual code, and code_desc is the description. Note this can be extended to any attribute requiring a description term.

ALL_10M

This table contains the natural log of the factorial of each number from 0 through 10,000,000. This table is called by wu4_function9biot to provide pre-generated factorials for computation of the first P-value from which to integrate (usually zero but accommodates highly skewed sets where zero is not a viable starting pint).

```
CREATE OR REPLACE PROCEDURE Factorial10
IS
    -- fills all_10M table with pairs of: number, LN(number!)
    i           NUMBER;
    last_i      NUMBER;
BEGIN
    INSERT INTO ALL_10M
        VALUES (0, 0); -- 0!=1, ln(1)=0
    last_i := LN (1);
```

-continued

```
    FOR i IN 1 .. 10000000
    LOOP
        INSERT INTO ALL_10M
            VALUES (i, LN (i) + (last_i));
        last_i := LN (i) + last_i;
            IF i/100000=ROUND(i/100000) THEN
            COMMIT;
        dbms_output.put_line( i );
        END IF;
    END LOOP;
    COMMIT;
END Factorial10;
/
===========================
CREATE TABLE ALL_10M
(
    NUMBER_OF_INTEREST NUMBER      NOT NULL,
    LN_FACTORIAL    NUMBER         NOT NULL,
    CONSTRAINT PK_ALL_10M
PRIMARY KEY
(NUMBER_OF_INTEREST)
)
ORGANIZATION INDEX
NOLOGGING;
```

Clustered Outcomes Processing Example

A client is interested in the outcomes associated with the population of patients taking thyroid hormones prior to their initiation date on the Ketek/Biaxin drug pair. The user creates the filter "IN Thyroid hormones" and applies it to "Dx OUT" in the data mining section for the Ketek/Biaxin drug pair.

Process will then commence in multiple stages (in order of operation):

Identify, aggregate, join and filter attribute/outcome pairs

1. Identify the population "in play" for the analysis, e.g., those taking thyroid hormones in the baseline period.

2. Collect all attributes belonging to these individuals in the appropriate pre-joined CLUSTER_BASELINE_POPS partition 3. Aggregate this set counting unique patients in each attribute a. We'll call this Set "A" (Nd and Nc counts for each attribute)

Set "A"—steps 1, 2, 3, 3a:

```
    SELECT attribute,attribute_value
        ,COUNT (UNIQUE CASE WHEN groupflag=1 THEN newindv_id
ELSE NULL END) nd
        ,COUNT (UNIQUE CASE WHEN groupflag=0 THEN newindv_id
ELSE NULL END) nc
        FROM
        CLUSTER_BASELINE_POPS WHERE product_id=2 AND
            version id=200503
--
        AND newindv_id IN ( select distinct newindv_id from rx_baseline
            where
drug_desc like '%thyroid hormones%') - could be drug class, NDC codes,
etc.
        GROUP BY attribute,attribute_value;
```

4. Create a placeholder attribute called "Baseline" and collect all attributes belonging to these individuals in the appropriate pre-joined CLUSTER_ BASELINE_POPS partition (using GENDER to prune)

5. Aggregate this set counting unique patients in the "Baseline"

a. We'll call this Set "B" (Nd and Nc counts for "Baseline", i.e. filter only attribute)

Set "B"—steps 4, 5, 5a:

```
    SELECT attribute,attribute_value,SUM(nd) nd,SUM(nc) nc FROM
    (
        SELECT 'Baseline' attribute,' ' attribute_value
        ,COUNT (UNIQUE CASE WHEN groupflag=1 THEN newindv_id
ELSE NULL END) nd
        ,COUNT (UNIQUE CASE WHEN groupflag=0 THEN newindv_id
ELSE NULL END) nc
        FROM
        CLUSTER_BASELINE_POPS WHERE product_id=2 AND
            version_id=200503
AND
        attribute='GENDER' AND newindv_id IN ( select distinct newindv_id
            from
rx_baseline where drug_desc like '%thyroid hormones%') - could be drug
class, NDC codes, etc.
        GROUP BY attribute,attribute_value
```

6. Merge Sets "A" and "B" into Set "AB" (all Nd and Nc counts)

UNION the two sets together and tag the combined set nd_nc. We have now generated the counts for every possible attribute.

7. Collect all permutation sets belonging to these individuals in the appropriate pre-joined CLUSTER_XD_XC_PRE-JOIN_DX_OP partition. Now let's collect the outcome sets and count the outcome population for each attribute/outcome pair.

8. Aggregate this set counting unique patients in each attribute/outcome pairing a. This becomes Cluster Set "C" (Xd and Xc counts for each attribute/outcome pair)

```
    Set "C"
    SELECT attribute,attribute_value,outcome_class,outcome_type
        ,COUNT (UNIQUE CASE WHEN groupflag=1 THEN newindv_id
        ELSE NULL
END) xd
        ,COUNT (UNIQUE CASE WHEN groupflag=0 THEN newindv_id
        ELSE NULL
END) xc
        FROM
        CLUSTER_XD_XC_PREJOIN_DX_OP -- one of three outcome
        tables
        WHERE product_id=2 AND version_id=200503 AND
        newindv_id IN ( select distinct newindv_id from rx_baseline where
            drug_desc
like '%thyroid hormones%') - could be drug class, NDC codes, etc.
        GROUP BY attribute,attribute_value,outcome_class,outcome_type
```

9. Create a placeholder attribute called "Baseline" and collect all outcome permutation sets belonging to these individuals in the appropriate pre-joined CLUSTER_XD_X-C_PREJOIN_DX_OP partition (using GENDER to prune). Again using GENDER to ensure a look at the entire baseline population we'll count the outcome population for each baseline/outcome pair.

10. Aggregate this set counting unique patients in each "Baseline"/outcome pairing a. This becomes Cluster Set "D" (Xd and Xc counts for each "Baseline"/outcome pair)

```
    Set "D"
    SELECT attribute,
    attribute_value,outcome_class,outcome_type,SUM(xd)
    xd,SUM(xc) xc
    FROM (
        SELECT 'Baseline' attribute,' '
    attribute_value,outcome_class,outcome_type
        ,COUNT (UNIQUE CASE WHEN groupflag=1 THEN newindv_id
        ELSE NULL
```

-continued

```
END) xd
    ,COUNT (UNIQUE CASE WHEN groupflag=0 THEN newindv_id
      ELSE NULL
END) xc
    FROM
    CLUSTER_XD_XC_PREJOIN_DX_OP -- one of three outcome
    tables
    WHERE product_id=2 AND version_id=200503 AND
    attribute='GENDER' --
    Attach filter here AND newindv_id IN ( select distinct newindv_id
    from
rx_baseline where drug_desc like '%thyroid hormones%') - could be
    drug class, NDC
codes, etc.
    GROUP BY attribute,attribute_value,outcome_class,outcome_type
    ) GROUP BY attribute,
    attribute_value,outcome_class,outcome_type
```

11. Merge Sets "C" and "D" into Set "CD" (all Xd and Xc count).

Merge the two sets using a UNION and tag as xd_cd

12. Join Set "AB" to Set "CD" by attribute becoming Set "ABCD" Where Sets "A" and "C" form the clustered outcomes while sets "B" and "D" comprise the dynamic baseline.

13. Discard trivial cases keeping only rows where nd>3 AND nc>3 AND (xd+xc)>3 AND ((nc+nd)−(xc+xd))>3

Using the code below, one can join the two sets (into "ABCD") and eliminate trivial cases (this is optional if one wants to keep and process such cases).

WHERE nd_nc.attribute=xd_xc.attribute AND
nd_nc.attribute_value=xd_xc.attribute_value AND nd>3 AND nc>3 AND
(xd+xc)>3 AND ((nc+nd)−(xc+xd))>3

14. Process RR and Yates CI for Set "ABCD".

15. Suppress processing of uninteresting cases, processing only those where POWER(ABS (xd−(xd+xc)*nd/(nd+nc))−0.5,2)>=(4*(xd+xc)*nd/(nd+nc)*(1−nd/(nd+nc))) (this is not done at step 13 due to an Oracle nuance)

Begin Cumulative Hypergeometric computation (AKA cdf)

16. Pass Xprime, Nprime, Xtot, Ntot rows from Set "ABCD" into the Oracle function wu4_function9biot The code below works with the population sets in the attribute outcome pairs generated in steps 1 to 13. Drug and comparator values are swapped prior to hypergeometric computation if the comparator has the stronger outcome signal. The log 10 value of these signals are demarked with a flipped score_sign. Prior to the hypergeometric calculation Wu4_funtion9biot( ) a case statement performs a secondary filter on uninteresting cases (those that will not have a significant score). This case statement can be removed if all cases are desired to be processed. The Relative Risk and Yates confidence interval are also processed in the code as supplementary information on the population set. The scores from the hypergeometric are converted by log 10 for readability but can be show in their original form if desired.

```
    d.attribute,d.attribute_value,a.code_desc "Attribute value
    desc",d.outcome_class,d.outcome_type,o.code_desc "Outcome type
    desc",d.xd,d.nd,d.xc,d.nc,
    CASE WHEN d.xc>0 THEN TO_CHAR( d.xd*d.nc/(d.xc*d.nd),'9999990.9')
ELSE
    '--' END rr,
    CASE WHEN (x−plower*x)>0 THEN (plower*x/d.nd)/((x−plower*x)/d.nc) ELSE
0
    END rrlower,
    CASE WHEN (x−pupper*x)>0 THEN (pupper*x/d.nd)/((x−pupper*x)/d.nc) ELSE
0
    END rrupper,
    CASE WHEN cumul_hyper>1e−128 THEN
    score_sign*TRUNC(LOG(10,d.cumul_hyper)) ELSE −10*score_sign END score
    FROM
    (
    SELECT c.*,(−b_high+SQRT(POWER(b_high,2)−4*a*c_high))/(2*a)
    pupper,(−b_low−SQRT(POWER(b_low,2)−4*a*c_low))/(2*a) plower,
    CASE WHEN POWER(ABS(xd−(xd+xc)*nd/(nd+nc))−.5,2) >=
    (8*(xd+xc)*nd/(nd+nc)*(1−nd/(nd+nc))) THEN
    aperio.Wu4_Function9biot(x_prime,n_prime,xd+xc,nd+nc) ELSE 1 END
    cumul_hyper
    FROM
    (
    SELECT b.*,1+d a,−2*pd_low−d b_low,−2*pd_high−d b_high,POWER(pd_low,2)
    c_low,POWER(pd_high,2) c_high FROM (
    SELECT a.*,xd+xc x,POWER(1.96,2)/(xd+xc) d,(Xd−.5)/(xd+xc)
    pd_low,(Xd+.5)/(xd+xc) pd_high FROM
    (
    SELECT
    nd_nc.attribute,nd_nc.attribute_value,xd_xc.outcome_class,xd_xc.outcome_
    type,xd_xc.xd,nd_nc.nd,xd_xc.xc,nd_nc.nc
    ,CASE WHEN xd>(xd+xc)*nd/(nd+nc) THEN xc ELSE xd END x_prime
    ,CASE WHEN xd>(xd+xc)*nd/(nd+nc) THEN nc ELSE nd END n_prime
    ,CASE WHEN xd>(xd+xc)*nd/(nd+nc) THEN −1 ELSE CASE WHEN xd=
    (xd+xc)*nd/(nd+nc) THEN 0 ELSE 1 END END score_sign
    FROM
    Set "ABCD"
```

17. Wu4_function9biot will determine if the tail starting point is zero or some other value (for sets where zero is not valid)

a. For a zero tail start the natural log of the hypergeometric is computed directly in the A11_10M SQL call per the Wu (2.1) equation b. For a non-zero tail start the natural log of the hypergeometric is computed directly in the A11_10M SQL call per the Wu (1.8) equation 18. These tail starting points are then recursively computed and summed up to the natural log Xprime value per the Wu (1.2) equation. The ln(cdf) is then converted to cdf using EXP( ) and truncated to an integer value.

Output Filtering for Score and Dynamic Baseline

At this point in the processing the data set contains inter-mingled scored values for both clustered outcomes and dynamic baseline data.

19. Re-calculate the dynamic baseline Set "BD" as above for use as a comparison source. Set "BD" is processed and scored. This step is not necessary unless (as shown) one wants to implement logic such as "discard any outcomes sets where the baseline data scores higher than the sub-cluster". Note that some of these sets (e.g., "B" and "D") can be written to use alternate methods of holding the processed data for later use in the query. Some of these include global temp tables, WITH temp AS, and other constructs that can pool sets into memory/disk can be used to curtail the reprocessing of the baseline sets.

20. Filter out rows in Set "ABCD" that have scores below 3.

21. Remove clustered outcome rows with scores >=3 if the dynamic baseline score is equal to or exceeds the clustered outcome score for a given outcome. The following code section is optional and serves the purpose of tagging the attributes and outcomes with descriptive information, showing only scores with an absolute values 3 or greater, and discarding outcome sets that have a lower score than their baseline counterparts.

```
) d, ALL_CODE_XWALK a,ALL_CODE_XWALK o
...
WHERE nd>3 AND nc>3 AND (xd+xc)>3 AND ((nc+nd)-(xc+xd))>3
```

-continued

```
AND
POWER(ABS(xd-(xd+xc)*nd/(nd+nc))-.5,2) >=
(8*(xd+xc)*nd/(nd+nc)*(1-nd/(nd+nc))) -- purposeful Cartesian since the
top IV returns one row
)) c -- one of three base score tables for filter
WHERE SUBSTR(d.attribute,1,2)=a.code_type(+) AND
d.attribute_value=a.code_set(+) AND
SUBSTR(d.outcome_class,1,2)=o.code_type(+) AND
d.outcome_type=o.code_set(+)
AND d.outcome_class= c.outcome_class AND
d.outcome_type=c.outcome_type
AND ABS(CASE WHEN cumul_hyper>1e-128 THEN
score_sign*TRUNC(LOG(10,cumul_hyper)) ELSE -10*score_sign
END)>ABS(c.score)
AND ABS(CASE WHEN cumul_hyper>1e-128 THEN
score_sign*TRUNC(LOG(10,cumul_hyper))
ELSE -10*score_sign END)>=3
```

Example 2

The "master sql" in Example 3 accesses SSTs and combines them into attribute/outcome population sets. It then processes these sets into hypergeometric scores, relative risk and Yates confidence intervals as shown in steps 1 through 21 above.

Example 4 creates the SSTs for use by the master SQL. These SSTs are packed by newind_id so the population set in play can be quickly retrieved. This is accomplished for cluster_baseline_pops by the SQL.

SELECT DISTINCT base.product_id,base.version_id,base.newindv_id,base.groupflag,base.attribute,base.attri bute_value FROM (merged sets)

The first two terms (product_id, version_id) land the data in a partition and the newindv_id field then clusters the data by individual. This SST packing could also be accomplished by using an ORDER BY clause, group by clause, a large concatenated index containing all the terms, or by using an index organized table.

Below, aspects of this example are explained in more detail. Let's step through some of the nuances in the creation of the CLUSTER_BASELINE_POPS table. This table is used to supply counts of the population in any attribute set and via the SST structure will quickly provide processing code with the desired individual's attributes for rapid counting.

```
INSERT /*+append*/ INTO CLUSTER_BASELINE_POPS
SELECT DISTINCT
base.product_id,base.version_id,base.newindv_id,base.groupflag,base.attr
ibute,base.attribute_value
FROM
>>>>>This section identifies and tags individuals that were active at least
>>>>>one day in the outcome period (the vast majority). The tag value '1 to
>>>>>7 days' will >>>>>be used as an independent attribute and treated in
>>>>>the code as if were a "typical" attribute like gender, age, taking drug
>>>>>"A", etc. during the baseline period.
SELECT product_id,version_id,b.NEWINDV_ID,b.groupflag,'Days since first
dispensing' attribute, '1 to 7 days' attribute_value,1 beginning,7
ending
FROM COHORT b WHERE b.match=1 AND b.termdate-b.indexdt >=1 AND
product_id=1
AND version_id=200503
UNION
>>>>> We'll append on another section for those active at least 8 days into
>>>>> the outcome period. etc for other days into segments
SELECT product_id,version_id,b.NEWINDV_ID,b.groupflag,'Days since first
dispensing' attribute, '8 to 29 days' attribute_value,8 beginning,29
ending
FROM COHORT b WHERE b.match=1 AND b.termdate-b.indexdt >=8 AND
product_id=1
AND version_id=200503
>>>>> Now we'll populate the gender attribute holding "Male or Female" in
```

```
     >>>>> the attribute_value
     SELECT product_id,version_id,NEWINDV_ID,groupflag,'GENDER'
attribute,sex
     attribute_value ,0 beginning,99999 ending
     FROM COHORT WHERE match=1 AND product_id=1 AND
version_id=200503
     UNION
     >>>>> Likewise for age or age_group (age can be grouped into logical ranges
     >>>>> as desired),
     SELECT product_id,version_id,NEWINDV_ID,groupflag,'AGE_GROUP'
     attribute,b.AGE_GROUP_name attribute_value ,0 beginning,99999 ending
     FROM COHORT a, AGE_GROUP b WHERE a.AGE BETWEEN
b.AGE_GROUP_START_YR AND
     b.AGE_GROUP_END_YR AND a.match=1 AND product_id=1 AND
version_id=200503
     UNION
     >>>>> Now codesets like diagnosis, procedure, prescription can be tagged
     >>>>> (diagnosis shown). Medical code sets can be either actual codes,
     >>>>> truncated codes, classes of codes, etc. There is no limitation on how
     >>>>> an attribute can be classified.
     SELECT product_id,version_id,NEWINDV_ID,groupflag,'DX Baseline'
     attribute,dx
     attribute_value ,0 beginning,99999 ending FROM DXBASE WHERE match=1
AND
     product_id=1 AND version_id=200503 AND indexflag=0 and drhlinpat=1
     >>>> Note ANY attribute can be presented in this format including but not
     >>>> limited to race, ethnicity, genetic information, family history,
     >>>> height, weight, profession, smoker, etc.
```

Let's step through some of the nuances in the creation of the CLUSTER_XD_XC_PREJOIN_DX_OP table (The other outcome tables are similar). The purpose of this table is to permeate all possible attribute with all possible outcomes individual by individual. Each attribute/outcome pair is tagged by an individual id. This allows for complete flexibility when including or excluding sets of individuals by any desired criteria (single or multiple).

```
     >>>> again we are creating an SST using the distinct clause which will sort
     >>>> by field order. The first two fields in this case will define a
     >>>> partition and the newindv_id will cluster data into the blocks by
     >>>> individual.
     INSERT /*+ append*/ INTO CLUSTER_XD_XC_PREJOIN_DX_OP
     SELECT DISTINCT
     base.product_id,base.version_id,base.newindv_id,base.groupflag,base.attr
     ibute,base.attribute_value,emergent.outcome_class,emergent.outcome_type,
     emergent.days_in_study
     FROM
     >>>> Outcomes will be expressed in terms of base attributes so this table
     >>>> will fist find attributes much like what was done in
     >>>> cluster_baseline_pops. However this time we will tag each
     >>>> attribute/outcome pair with an individual_id instead of just each
     >>>> attribute with an individual_id.
     >>>> This section is finding the outcomes for each person based on when the
     >>>> outcome occurred. Each persons attribute are then permeated by that
     >>>> person's outcomes via the join "base.newindv_id=emergent.newindv_id"
     >>>> and placed in the appropriate time range "emergent.days_in_study
     BETWEEN
     >>>> base.beginning AND base.ending". Note in this example the Dx codes are
     >>>> truncated to widen the outcome group. This is optional depending on the
     >>>> desired outcome granularity. Also we only use matched patients to
     >>>> mitigate confounding of the results where each person in the study set
     >>>> requires a pair sharing key attribute characteristics.
     (SELECT DISTINCT product_id, version_id, a.newindv_id, a.groupflag,
     'DX_OUTPATIENT' outcome_class,
     CASE
     WHEN LENGTH (TRIM (a.dx_emerg)) = 4
     AND SUBSTR (dx_emerg, 1, 1) <> 'E'
     THEN SUBSTR (dx_emerg, 1, 3)
     ELSE TRIM (dx_emerg)
     END outcome_type,
     days_in_study
     FROM dxemerg a
     WHERE a.match = 1
     AND a.product_id=1
     AND a.version_id = 200503
     AND siteflag = 2 ) emergent
     WHERE base.newindv_id=emergent.newindv_id AND emergent.days_in_study
```

```
BETWEEN
    base.beginning AND base.ending;
```

As described earlier, these tables can be used to quickly process and "score" massive permutation sets of attribute/outcome pairs. Statistically interesting combinations can easily by floated to the top by sorting on score. Coupled with the filtering capability to select any sub-population this question can be extended into:

Are women who are on thyroid medications more likely to have headaches when taking drug "A" than drug "B"?

Are males between 50 and 59 who have had bypass surgery more likely to have strokes when taking drug "A" than drug "B"

Does drug "B" have an unforeseen benefit in reducing a common disease in women who live in the south (e.g. Sinusitis)?

This powerful technique can also be extended to attribute sub clusters and outcome pairs (AKA syndromes). In other words we can permeate every combination of attributes and find these important pieces of information and float them to the top automatically. Also, pair of outcomes can be automatically coupled into syndromes and mined. This sub-attribute clustering can also be coupled with syndromes to mine and score for information as complex as:

Women taking NSAIDs are more likely to show headache and vomiting when taking drug "B" vs drug "A". In other words, with no filtering criteria the previously mentioned attribute/outcome pairs would automatically score the following sets.

Set#1 Drug "A" vs. Drug "B"—Women experiencing headache

Set#2 Drug "A" vs. Drug "B"—Women experiencing vomiting

Set#3 Drug "A" vs. Drug "B"—All on NSAIDs experiencing headache

Set#4 Drug "A" vs. Drug "B"—All on NSAIDs experiencing vomiting

The sub-cluster sets and syndrome processing would also test, score and present:

Set#5 Drug "A" vs. Drug "B"—Women on NSAIDs experiencing headache

Set#6 Drug "A" vs. Drug "B"—Women on NSAIDs experiencing vomiting

Set#7 Drug "A" vs. Drug "B"—Women on NSAIDs experiencing headache and vomiting

Set#8 Drug "A" vs. Drug "B"—Women experiencing headache and vomiting

Set#9 Drug "A" vs. Drug "B"—All on NSAIDs experiencing headache and vomiting

Set#10 Drug "A" vs. Drug "B"—Women experiencing headache and vomiting

The example below walks through the generation of set#5 and set#6 (and all other possible permutations of attribute1/attribute2/outcome triplets)

By sourcing the CLUSTER_BASELINE_POPS table twice, one can create and store all attribute sub-cluster permutations as shown below into table ALLPROD2b_DOUBLET_NS. This table contains the attribute/attribute counts.

```
CREATE TABLE ALL_PROD2b_DOUBLET_NS AS
    SELECT a.ATTRIBUTE a1, a.ATTRIBUTE_VALUE
    av1,b.ATTRIBUTE a2,
    b.ATTRIBUTE_VALUE av2
    ,COUNT(UNIQUE CASE WHEN a.groupflag=1 THEN
    a.newindv_id ELSE
NULL END)
    nd
    ,COUNT(UNIQUE CASE WHEN a.groupflag=0 THEN
    a.newindv_id ELSE
NULL END )
    nC
    FROM
    CLUSTER_BASELINE_POPS a,CLUSTER_BASELINE_POPS b
    WHERE a.product_id=2 AND b.product_id=2
    AND /* a.ATTRIBUTE_VALUE='F' AND
    b.attribute_value='WEST' AND */
    a.attribute||a.attribute_value>b.attribute||b.attribute_value AND
    a.newindv_id=b.newindv_id /*AND
    a.attribute_value>b.attribute_value
    don't
    double return set*/
    GROUP BY a.ATTRIBUTE ,
    a.ATTRIBUTE_VALUE,b.ATTRIBUTE,
    b.ATTRIBUTE_VALUE
    HAVING COUNT(UNIQUE CASE WHEN a.groupflag=1 THEN
    a.newindv_id
ELSE NULL
    END)>3 AND COUNT(UNIQUE CASE WHEN a.groupflag=0
    THEN
a.newindv_id ELSE
    NULL
    END ) >3
```

Now we can create the complimentary table containing all the outcomes counts for each attribute/attribute pair. This table contains the attribute/attribute outcome counts.

```
CREATE TABLE ALL_PROD2b_DOUBLET_XS
SELECT * FROM
(
SELECT a1,av1,a2,av2 ,outcome_class,outcome_type
    ,COUNT(UNIQUE CASE WHEN groupflag=1 THEN newindv_id ELSE NULL
END) xd
    ,COUNT(UNIQUE CASE WHEN groupflag=0 THEN newindv_id ELSE NULL
END ) xC
    FROM
    (
    SELECT x.attribute a1,x.attribute_value av1,y.attribute
    a2,y.attribute_value
    av2,x.outcome_class,x.outcome_type,x.newindv_id,x.groupflag FROM
    (
    SELECT DISTINCT
```

```
    a.ATTRIBUTE,a.ATTRIBUTE_VALUE,a.outcome_class,a.outcome_type,
    newindv_id,groupflag
    FROM CLUSTER_XD_XC_PREJOIN_DX_OP a WHERE a.PRODUCT_ID=2 )
x,
    (
    SELECT DISTINCT
    a.ATTRIBUTE,a.ATTRIBUTE_VALUE,a.outcome_class,a.outcome_type,newindv_id,
    groupflag
    FROM CLUSTER_XD_XC_PREJOIN_DX_OP a WHERE a.PRODUCT_ID=2 )
y
    WHERE x.attribute||x.attribute_value>y.attribute||y.attribute_value AND
    x.newindv_id=y.newindv_id /* don't double return set*/
    AND x.outcome_class=y.outcome_class AND x.outcome_type=y.outcome_type
)
    GROUP BY a1,av1,a2,av2 ,outcome_class,outcome_type
    )
```

These two tables can then be combined and scored often yielding powerful insight into hidden attribute combinations that have interesting properties.

```
CREATE TABLE spir_dx_ip_doublet_scores AS
SELECT iv2.*, CASE WHEN
POWER(ABS(xd-(xd+xc)*nd/(nd+nc))-.5,2) >=
(4*(xd+xc)*nd/(nd+nc)*(1-nd/(nd+nc))) THEN
Wu4_Function9biot(x_prime,n_prime,xd+xc,nd+nc) ELSE 1 END
cumul_hyper
FROM
(
SELECT iv.*,a.nd,a.nc
,CASE WHEN xd>(xd+xc)*nd/(nd+nc) THEN xc ELSE xd END
x_prime
,CASE WHEN xd>(xd+xc)*nd/(nd+nc) THEN nc ELSE nd END
n_prime
,CASE WHEN xd>(xd+xc)*nd/(nd+nc) THEN -1 ELSE CASE
WHEN xd=
(xd+xc)*nd/(nd+nc) THEN 0 ELSE 1 END END score_sign
FROM
ALL_PROD2b_DOUBLET_XS iv,ALL_PROD2b_DOUBLET_NS a
WHERE iv.a1=a.a1 AND iv.a2=a.a2 AND iv.av1=a.av1 AND
iv.av2=a.av2 AND
(xd+xc)>3 AND nd>3 AND nc>3 AND ((nc + nd) − (xc + xd)) >
3 AND
POWER(ABS(xd-(xd+xc)*nd/(nd+nc))-.5,2) >=
(4*(xd+xc)*nd/(nd+nc)*(1-nd/(nd+nc)))
) iv2 ORDER BY cumul_hyper ASC
```

Example 3

Master Sql, Including Hypergeometric Call

```
SELECT * FROM
(
SELECT 2 product_id,200503 version_id,
d.attribute,d.attribute_value,a.code_desc "Attribute value
desc",d.outcome_class,d.outcome_type,o.code_desc "Outcome type
desc",d.xd,d.nd,d.xc,d.nc,
CASE WHEN d.xc>0 THEN TO_CHAR( d.xd*d.nc/(d.xc*d.nd),'9999990.9') ELSE
'--' END rr,
CASE WHEN (x-plower*x)>0 THEN (plower*x/d.nd)/((x-plower*x)/d.nc) ELSE 0
END rrlower,
CASE WHEN (x-pupper*x)>0 THEN (pupper*x/d.nd)/((x-pupper*x)/d.nc) ELSE 0
END rrupper,
CASE WHEN cumul_hyper>1e-128 THEN
score_sign*TRUNC(LOG(10,d.cumul_hyper)) ELSE -10*score_sign END score
FROM
(
SELECT c.*,(-b_high+SQRT(POWER(b_high,2)-4*a*c_high))/(2*a)
pupper,(-b_low-SQRT(POWER(b_low,2)-4*a*c_low))/(2*a) plower,
CASE WHEN POWER(ABS(xd-(xd+xc)*nd/(nd+nc))-.5,2) >=
(8*(xd+xc)*nd/(nd+nc)*(1-nd/(nd+nc))) THEN
aperio.Wu4_Function9biot(x_prime,n_prime,xd+xc,nd+nc) ELSE 1 END
cumul_hyper
FROM
(
SELECT b.*,1+d a,-2*pd_low-d b_low,-2*pd_high-d b_high,POWER(pd_low,2)
c_low,POWER(pd_high,2) c_high FROM (
SELECT a.*,xd+xc x,POWER(1.96,2)/(xd+xc) d,(Xd-.5)/(xd+xc)
pd_low,(Xd+.5)/(xd+xc) pd_high FROM
(
SELECT
nd_nc.attribute,nd_nc.attribute_value,xd_xc.outcome_class,xd_xc.outcome_
type,xd_xc.xd,nd_nc.nd,xd_xc.xc,nd_nc.nc
,CASE WHEN xd>(xd+xc)*nd/(nd+nc) THEN xc ELSE xd END x_prime
,CASE WHEN xd>(xd+xc)*nd/(nd+nc) THEN nc ELSE nd END n_prime
,CASE WHEN xd>(xd+xc)*nd/(nd+nc) THEN -1 ELSE CASE WHEN xd=
(xd+xc)*nd/(nd+nc) THEN 0 ELSE 1 END END score_sign
```

-continued

```
FROM
(
SELECT attribute,attribute_value
,COUNT (UNIQUE CASE WHEN groupflag=1 THEN newindv_id ELSE NULL END)
nd
,COUNT (UNIQUE CASE WHEN groupflag=0 THEN newindv_id ELSE NULL END)
nc
FROM
CLUSTER_BASELINE_POPS WHERE product_id=2 AND version_id=200503 --
Attach filter here AND newindv_id IN ( )
GROUP BY attribute,attribute_value
UNION
SELECT attribute,attribute_value,SUM(nd) nd,SUM(nc) nc FROM
(
SELECT 'Baseline' attribute,'' attribute_value
,COUNT (UNIQUE CASE WHEN groupflag=1 THEN newindv_id ELSE NULL END)
nd
,COUNT (UNIQUE CASE WHEN groupflag=0 THEN newindv_id ELSE NULL END)
nc
FROM
CLUSTER_BASELINE_POPS WHERE product_id=2 AND version_id=200503 AND
attribute='GENDER' -- Attach filter here AND newindv_id IN ( )
GROUP BY attribute,attribute_value
) GROUP BY attribute,attribute_value
) nd_nc
,
(
SELECT attribute,attribute_value,outcome_class,outcome_type
,COUNT (UNIQUE CASE WHEN groupflag=1 THEN newindv_id ELSE NULL END)
xd
,COUNT (UNIQUE CASE WHEN groupflag=0 THEN newindv_id ELSE NULL END)
xc
FROM
CLUSTER_XD_XC_PREJOIN_DX_OP -- one of three outcome tables
WHERE product_id=2 AND version_id=200503 -- Attach filter here AND
newindv_id IN ( )
GROUP BY attribute,attribute_value,outcome_class,outcome_type
UNION
SELECT attribute, attribute_value,outcome_class,outcome_type,SUM(xd)
xd,SUM(xc) xc
FROM (
SELECT 'Baseline' attribute,''
attribute_value,outcome_class,outcome_type
,COUNT (UNIQUE CASE WHEN groupflag=1 THEN newindv_id ELSE NULL END)
xd
,COUNT (UNIQUE CASE WHEN groupflag=0 THEN newindv_id ELSE NULL END)
xc
FROM
CLUSTER_XD_XC_PREJOIN_DX_OP -- one of three outcome tables
WHERE product_id=2 AND version_id=200503 AND attribute='GENDER' --
Attach filter here AND newindv_id IN ( )
GROUP BY attribute,attribute_value,outcome_class,outcome_type
) GROUP BY attribute, attribute_value,outcome_class,outcome_type
) xd_xc
WHERE nd_nc.attribute=xd_xc.attribute AND
nd_nc.attribute_value=xd_xc.attribute_value AND nd>3 AND nc>3 AND
(xd+xc)>3 AND ((nc+nd)−(xc+xd))>3
) a
) b
) c
) d, ALL_CODE_XWALK a,ALL_CODE_XWALK o
(
SELECT outcome_class,outcome_type,CASE WHEN
POWER(ABS(xd−(xd+xc)*nd/(nd+nc))−.5,2) >=
(8*(xd+xc)*nd/(nd+nc)*(1−nd/(nd+nc))) THEN
score_sign*TRUNC(LOG(10,GREATEST(aperio.Wu4_Function9biot(x_prime,n_prim
e,xd+xc,nd+nc), 1e−128))) ELSE 0 END score
FROM
(SELECT
nd_nc.attribute,nd_nc.attribute_value,xd_xc.outcome_class,xd_xc.outcome_
type,xd_xc.xd.nd_nc.nd,xd_xc.xc,nd_nc.nc
,CASE WHEN xd>(xd+xc)*nd/(nd+nc) THEN xc ELSE xd END x_prime
,CASE WHEN xd>(xd+xc)*nd/(nd+nc) THEN nc ELSE nd END n_prime
,CASE WHEN xd>(xd+xc)*nd/(nd+nc) THEN −1 ELSE CASE WHEN xd=
(xd+xc)*nd/(nd+nc) THEN 0 ELSE 1 END END score_sign
FROM
(
SELECT attribute,attribute_value,SUM(nd) nd,SUM(nc) nc FROM
(
```

```
SELECT 'Baseline' attribute,'' attribute_value
,COUNT (UNIQUE CASE WHEN groupflag=1 THEN newindv_id ELSE NULL END)
nd
,COUNT (UNIQUE CASE WHEN groupflag=0 THEN newindv_id ELSE NULL END)
nc
FROM
CLUSTER_BASELINE_POPS WHERE product_id=2 AND version_id=200503 AND
attribute='GENDER' -- Attach filter here AND newindv_id IN ( )
GROUP BY attribute,attribute_value
) GROUP BY attribute,attribute_value
) nd_nc
,
(
SELECT attribute, attribute_value,outcome_class,outcome_type,SUM(xd)
xd,SUM(xc) xc
FROM (
SELECT 'Baseline' attribute,''
attribute_value,outcome_class,outcome_type
,COUNT (UNIQUE CASE WHEN groupflag=1 THEN newindv_id ELSE NULL END)
xd
,COUNT (UNIQUE CASE WHEN groupflag=0 THEN newindv_id ELSE NULL END)
xc
FROM
CLUSTER_XD_XC_PREJOIN_DX_OP -- one of three outcome tables
WHERE product_id=2 AND version_id=200503 AND attribute='GENDER' --
Attach filter here AND newindv_id IN ( )
GROUP BY attribute,attribute_value,outcome_class,outcome_type
) GROUP BY attribute, attribute_value,outcome_class,outcome_type
) xd_xc
WHERE nd>3 AND nc>3 AND (xd+xc)>3 AND ((nc+nd)-(xc+xd))>3 AND
POWER(ABS(xd-(xd+xc)*nd/(nd+nc))-.5,2) >=
(8*(xd+xc)*nd/(nd+nc)*(1-nd/(nd+nc))) -- purposeful cartesian since the
top IV returns one row
)) c -- one of three base score tables for filter
WHERE SUBSTR(d.attribute,1,2)=a.code_type(+) AND
d.attribute_value=a.code_set(+) AND
SUBSTR(d.outcome_class,1,2)=o.code_type(+) AND
d.outcome_type=o.code_set(+)
AND d.outcome_class=c.outcome_class AND d.outcome_type=c.outcome_type
AND ABS(CASE WHEN cumul_hyper>1e-128 THEN
score_sign*TRUNC(LOG(10,cumul_hyper)) ELSE -10*score_sign
END)>ABS(c.score)
AND ABS(CASE WHEN cumul_hyper>1e-128 THEN
score_sign*TRUNC(LOG(10,cumul_hyper)) ELSE -10*score_sign END)>=3
```

Example 4

Filename: r4product_id1_opiprx.sql

SELECT 'DONE 1' FROM DUAL;

Example 5

Techniques of this disclosure address a number of challenges in data manipulation encountered in both the medical space and other areas.

Data Acquisition

All Attributes and outcomes may be stored in a coded manner that allows complete flexibility to accommodate all manner of terms (e.g., attributes like "Male", "Valium" and "Age" can occupy the same attribute field and be processed identically). SSTs provider rapid working sets of data, reducing physical I/Os by presenting the data in a "rich" format where each database block holds many rows of the desired data. For cluster investigations, SSTs can be created that hold all possible attribute/outcome permutation sets. Sub-clusters (double attributes) and syndromes (double outcomes) can also be processed if desired.

Data Reduction

Logarithms may be used in both the generation of the initial recursion point (logarithmic factorial table) and in the recurring of successive terms (to avoid over/under flow). Attribute/outcome sets are quickly mingled and counted using the pre-permeated tables. Uninteresting cases may be filtered out prior to processing if desired.

Data Presentation

Scores sets can be presented to the user in order of signal strength. Geographic charts can be used to provider "bird's eye" views of disease clusters, provider clusters, and the trending of both.

| Problem (in order of explanation) | Example Solution |
|---|---|
| Attribute mixed forms (Male and DX = 250) | Create attribute table that allow co-mingling of all possible attribute types |
| Physical Disk I/Os required for data retrieval | Packed tables containing only the fields desired (DB blocks are "rich" and field-efficient) |
| Hash Join of attribute/outcomes | Pre-permeated (and packed) attribute/outcome table sets |
| Large number of permutation sets | Elimination of uninteresting sets prior to processing (per Walker input) |
| Hypergeometric: Numeric Over/under flow | Work entirely in logarithms |
| Hypergeometric: Factorial generation | Pre-generate, cached table of all factorials (values held in LOG form, 4 cached I/Os to create initial recursion point) |

Example 6

Alternate Coding

Inline Views Vs. Set Based

Though SQL set based operations (MINUS, UNION, INTERSECT) are fast, it is possible to realize even faster results if the set variables are limited to only those needed for the set based operation. For example, if one is interested in the gender distribution of patients with diabetes who are also on LIPITOR but have not had coronary bypass surgery in the last year, one can construct the SQL as below. A key point is that, in such an example, the "individual_id" is all that is required for the set intersection while "gender" is a piggyback variable defined as useful in segmenting the counts (e.g. male and female below). When the SQL is coded in this way, the database is forced to hash both patient_id and gender when checking for individuals in both sets. Gender is redundant and not needed for this particular comparison operation. After the comparisons are made, gender is need to count individuals in the various segments.

```
SELECT COUNT(UNIQUE a.individual_id) -- Set based (MINUS/INTERSECT)
,count(unique case when gender='M' then individual_id else null end) males
,count(unique case when gender='F' then individual_id else null end) females FROM (
Select individual_id, gender from attribute_table where attribute='DIABETES'
INTERSECT -- DB forced to process gender here Select individual_id, gender from
attribute_table where attribute='LIPITOR'
MINUS -- DB forced to process gender here Select individual_id, gender from
attribute_table where attribute='CABG'
)
    If, however, the SQL is coded with inline views as below, the database does not
have to match "gender" when determining valid individuals i.e. only using "gender" in
the final segmentation case statements. The predicate "WHERE
iv1.inidividual_id=iv2.individual_id" is more quickly doing the (above) INTERSECT
and the "WHERE NOT EXISTS..." is more quickly doing the (above) MINUS operation.
SELECT COUNT(UNIQUE a.individual_id) -- Set based (MINUS/INTERSECT)
,count(unique case when gender='M' then individual_id else null end) males
,count(unique case when gender='F' then individual_id else null end) females FROM (
Select iv1.individual_id,iv1.gender FROM (Select individual_id, gender from
attribute_table where attribute='DIABETES' )iv1 ,(Select individual_id, gender from
attribute_table where attribute='LIPITOR') iv2 WHERE
iv1.inidividual_id=iv2.individual_id ) iv12 WHERE NOT EXISTS SELECT 'X' FROM
attribute_table z WHERE z.attribute='CABG' and z.individual_id=iv12.individual_id
)
```

In practice the two approaches might appear as below. The inline view version gives the same results as the set based SQL and, in this example, returns the data four times faster than the set based SQL. Performance is likely to be even more pronounced between the two approaches if more piggyback variables are in play.

```
SELECT COUNT(UNIQUE a.individual_id) -- Set based (MINUS/INTERSECT)
,count(unique case when gender='M' then individual_id else null end) males
,count(unique case when gender='F' then individual_id else null end) females
,count(unique case when gender not in ('F','M') then individual_id else null end) unknown
FROM ( SELECT a.INDIVIDUAL_ID, a.DOB, a.GENDER, a.ZIP5, SUBSTR(a.ZIP5,
1, 3) ZIP3 FROM INDIVIDUAL_ID a WHERE a.CODE_KEY IN
('DX5053481','DX505348481','DX50534848481','DX50534848491','DX505348491','DX
505348511','DX50534851481','DX50534851491','DX505348551','DX505348561'
,'DX505348571','DX505351531','DX515355501','DX515450481','DX51545048491','DX
51545452491','DX535656491','DX545256481','DX54525648481','DX54525648491','DX
54525648501'
,'DX54525648511','DX54525648521','DX555553481','DX555553491','DX864956481','D
X865555491','PX65535348481','PX65535348491','PX65535348501','PX65535348511'
,'PX65535348521','PX65535348531','PX65535348541','PX65535348551','PX655353485
61','PX71484948561','PX71484948571','PX83574952481','PX83574952491'
,'PX83575253531','PX83575254481','PX83575254531','PX89525451481')
INTERSECT
SELECT a.INDIVIDUAL_ID, a.DOB, a.GENDER, a.ZIP5, SUBSTR(a.ZIP5, 1, 3) ZIP3
FROM INDIVIDUAL_ID a WHERE a.CODE_KEY IN ('RX-7101552337652', 'RX-
710155341', 'RX-7101554037652', 'RX-7101562337652', 'RX-7101564037652','RX-
7101572337652','RX-710157731','RX-7101582337652','RX-710158731')
MINUS
SELECT a.INDIVIDUAL_ID, a.DOB, a.GENDER, a.ZIP5, SUBSTR(a.ZIP5, 1, 3) ZIP3
FROM INDIVIDUAL_ID a WHERE a.CODE_KEY IN
('PX48485354541','PX51515349481','PX51515349491','PX51515349501','PX515153495
11','PX51515349521','PX51515349541','PX51515349551','PX51515349561'
,'PX51515349571','PX51515350491','PX51515350501','PX51515350511','PX515153515
11','PX51515351521','PX51515351531','PX51515351541')
) a
SELECT COUNT(UNIQUE individual_id) -- Inline View based ,count(unique case
when gender='M' then individual_id else null end) males ,count(unique case when
```

```
gender='F' then individual_id else null end) females ,count(unique case when gender not
in ('F','M') then individual_id else null end) unknown FROM ( SELECT
a.individual_id,a.gender FROM ( SELECT a.INDIVIDUAL_ID, a.DOB, a.GENDER,
a.ZIP5, SUBSTR(a.ZIP5, 1, 3) ZIP3 FROM INDIVIDUAL_ID a WHERE
a.CODE_KEY                                                                              IN
('DX5053481','DX505348481','DX50534848481','DX50534848491','DX505348491','DX
505348511','DX50534851481','DX50534851491','DX505348551','DX505348561'
,'DX505348571','DX505351531','DX515355501','DX515450481','DX51545048491','DX
51545452491','DX535656491','DX545256481','DX54525648481','DX54525648491','DX
54525648501'
,'DX54525648511','DX54525648521','DX555553481','DX555553491','DX864956481','D
X865555491','PX65535348481','PX65535348491','PX65535348501','PX65535348511'
,'PX65535348521','PX65535348531','PX65535348541','PX65535348551','PX655353485
61','PX71484948561','PX71484948571','PX83574952481','PX83574952491'
,'PX83575253531','PX83575254481','PX83575254531','PX89525451481')
) a,
(
SELECT a.INDIVIDUAL_ID, a.DOB, a.GENDER, a.ZIP5, SUBSTR(a.ZIP5, 1, 3) ZIP3
FROM INDIVIDUAL_ID a WHERE a.CODE_KEY IN ('RX-7101552337652', 'RX-
710155341', 'RX-7101554037652', 'RX-7101562337652', 'RX-7101564037652','RX-
7101572337652','RX-710157731','RX-7101582337652', 'RX-710158731')
) b
WHERE a.individual_id=b.individual_id
) d WHERE NOT EXISTS (
SELECT 'X' FROM INDIVIDUAL_ID z WHERE z.CODE_KEY IN
('PX48485354541','PX51515349481','PX51515349491','PX51515349501','PX515153495
11'
,'PX51515349521','PX51515349541','PX51515349551','PX51515349561','PX515153495
71','PX51515350491','PX51515350501','PX51515350511','PX51515351511'
,'PX51515351521','PX51515351531','PX51515351541')
AND z.individual_id=d.individual_id);
```

With the benefit of the present disclosure, those having ordinary skill in the art will comprehend that techniques claimed here may be modified and applied to a number of additional, different applications, achieving the same or a similar result. The claims cover all such modifications that fall within the scope and spirit of this disclosure.

REFERENCES

Each of the following references is hereby incorporated by reference in its entirety:

U.S. Pat. No. 6,826,536
U.S. Pat. No. 6,732,113
U.S. Pat. No. 6,370,511
U.S. Pat. No. 6,253,186
U.S. Pat. No. 6,223,164
U.S. Pat. No. 6,151,581
U.S. Pat. No. 6,014,631
U.S. Pat. No. 5,970,464
U.S. Pat. No. 5,970,463
U.S. Pat. No. 5,956,689
U.S. Pat. No. 5,835,897
U.S. Pat. No. 5,557,514
U.S. Pat. No. 5,191,522
U.S. Patent Publication No. 20050234740
U.S. Patent Publication No. 20050228808
U.S. Patent Publication No. 20050228593
U.S. Patent Publication No. 20050203776
U.S. Patent Publication No. 20050114334
U.S. Patent Publication No. 20050071189
U.S. Patent Publication No. 20050010443
U.S. Patent Publication No. 20040260577
U.S. Patent Publication No. 20040249677
U.S. Patent Publication No. 20040236601
U.S. Patent Publication No. 20040210457
U.S. Patent Publication No. 20040172293
U.S. Patent Publication No. 20040093240
U.S. Patent Publication No. 20040078236
U.S. Patent Publication No. 20040078220
U.S. Patent Publication No. 20040078216
U.S. Patent Publication No. 20040044654
U.S. Patent Publication No. 20030065740
U.S. Patent Publication No. 20030046114
U.S. Patent Publication No. 20020173990
U.S. Patent Publication No. 20020165762
U.S. Patent Publication No. 20020138306
U.S. Patent Publication No. 20020077853
U.S. Patent Publication No. 20020002474
U.S. Patent Publication No. 20010034631
Walker, Alec; Detection Routine for Interesting Subgroups, *Data Mining for Aperio*, May 16, 2005
Wu, Trong; An Accurate Computation of the Hypergeometric Distribution Function, *ACM Transactions on Mathematical Software*, Vol 19, No. 1, March 1993, Pages 33-43.

What is claimed is:

1. A computer program product, comprising:
    a non-transitory computer readable medium comprising:
        code to search data;
        code to compare one subset of the data against a plurality of other subsets of the data; and
        code to calculate a hypergeometric statistical result based, at least in part, on the comparing step using one or more pre-generated factorial tables, the pre-generated factorial tables comprising logarithmic entries.

2. The computer program product of claim 1, further comprising code to detect fraud based, at least in part, on the calculated hypergeometric statistical result.

3. The computer program product of claim 1, further comprising code to perform quality control on the data.

4. The computer program product of claim 1, further comprising code to perform pattern recognition on the data.

5. The computer program product of claim 1, further comprising code to perform cluster validity analysis on the data.

6. The computer program product of claim 1, further comprising code to perform tree classifier design on the data.

7. The computer program product of claim 1, further comprising code to perform image template matching on the data.

8. The computer program product of claim 1, further comprising code to cluster the data into appropriate groupings before calculating the hypergeometric statistical result.

9. The computer program product of claim 1, further comprising code to present certain portions of the data to a user based, at least in part, on the calculated hypergeometric statistical result.

10. The computer program product of claim 1, wherein the code to calculate the hypergeometric statistical result comprises:
    code to calculate a starting probability distribution function (pdf) value; and
    code to recursively generate additional pdf values using the logarithmic entries.

11. The computer program product of claim 1, wherein the logarithmic entries comprise natural logarithmic entries.

12. The computer program product of claim 1, wherein the data comprises specialized search tables (SSTs), and the medium further comprises code to generate the specialized search tables (SSTs) by selecting particular data for inclusion in the specialized search tables (SSTs).

13. A method for statistical calculations based on administrative health claims data comprising:
    searching, with a computing device, data;
    comparing, with the computing device, one subset of the data against a plurality of other subsets of the data; and
    calculating, with the computing device, a hypergeometric statistical result based, at least in part, on the comparing step using one or more pre-generated factorial tables, the pre-generated factorial tables comprising logarithmic entries.

14. The method of claim 13, further comprising using the hypergeometric statistical result to detect medical-related fraud.

15. The method of claim 13, further comprising performing quality control on the data.

16. The method of claim 13, further comprising performing pattern recognition on the data.

17. The method of claim 13, further comprising performing cluster validity analysis on the data.

18. The method of claim 13, further comprising performing tree classifier design on the data.

19. The method of claim 13, further comprising performing image template matching on the data.

20. The method of claim 13, further comprising clustering the data into appropriate groupings before calculating the hypergeometric statistical result.

21. The method of claim 13, further comprising:
    calculating a starting probability distribution function (pdf) value; and
    recursively generating additional pdf values using the logarithmic entries.

22. The method of claim 13, wherein the logarithmic entries comprise natural logarithmic entries.

23. The method of claim 13, wherein the data comprises specialized search tables (SSTs), and the medium further comprises code to generate the specialized search tables (SSTs) by selecting particular data for inclusion in the specialized search tables (SSTs).

* * * * *